US008722123B2

(12) United States Patent
Doyle et al.

(10) Patent No.: US 8,722,123 B2
(45) Date of Patent: May 13, 2014

(54) ANTIMICROBIAL COMPOSITION AND USE AS FOOD TREATMENT

(75) Inventors: Michael P. Doyle, Peachtree City, GA (US); Tong Zhao, Peachtree City, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/363,455

(22) Filed: Feb. 1, 2012

(65) Prior Publication Data

US 2012/0148716 A1 Jun. 14, 2012

Related U.S. Application Data

(63) Continuation-in-part of application No. 12/811,560, filed as application No. PCT/US2009/044815 on May 21, 2009, now abandoned.

(60) Provisional application No. 61/055,299, filed on May 22, 2008, provisional application No. 61/085,050, filed on Jul. 31, 2008, provisional application No. 61/151,377, filed on Feb. 10, 2009, provisional application No. 61/446,082, filed on Feb. 24, 2011.

(51) Int. Cl.

| | |
|---|---|
| ***A23L 3/3463*** | (2006.01) |
| ***A23L 3/3508*** | (2006.01) |
| ***A01N 37/02*** | (2006.01) |
| ***A01N 25/04*** | (2006.01) |
| ***A01N 25/30*** | (2006.01) |
| ***A01N 41/02*** | (2006.01) |
| ***A01N 37/42*** | (2006.01) |
| ***A01N 37/36*** | (2006.01) |
| ***A23B 4/18*** | (2006.01) |
| ***B65B 55/00*** | (2006.01) |

(52) U.S. Cl.

USPC ........... 426/310; 426/326; 426/332; 426/335; 514/557

(58) Field of Classification Search

CPC ... A01N 2300/00; A01N 25/30; A01N 41/02; A01N 37/02; A01N 37/36; A01N 37/42; A01N 25/04; A23L 3/3463; A23L 3/3508; A23B 41/18; B65B 55/00

See application file for complete search history.

(56) References Cited

U.S. PATENT DOCUMENTS

| | | | |
|---|---|---|---|
| 4,842,593 | A | 6/1989 | Jordan et al. |
| 5,186,962 | A | 2/1993 | Hutkins et al. |
| 5,308,615 | A | 5/1994 | DeLoach et al. |
| 5,451,369 | A | 9/1995 | Daeschel et al. |
| 5,498,295 | A | 3/1996 | Murch et al. |
| 5,500,048 | A | 3/1996 | Murch et al. |
| 5,500,143 | A | 3/1996 | Murch et al. |
| 5,503,764 | A | 4/1996 | Murch et al. |
| 5,549,758 | A | 8/1996 | Murch et al. |
| 5,705,461 | A | 1/1998 | Murch et al. |
| 5,849,678 | A | 12/1998 | Murch et al. |
| 5,869,066 | A | 2/1999 | Pace et al. |
| 5,932,527 | A | 8/1999 | Roselle et al. |
| 5,965,499 | A | 10/1999 | Murch et al. |
| 5,972,857 | A | 10/1999 | Roselle et al. |
| 5,994,383 | A | 11/1999 | Dyer et al. |
| 5,997,654 | A | 12/1999 | Murch et al. |
| 6,080,401 | A | 6/2000 | Reddy et al. |
| 6,345,634 | B1 | 2/2002 | Murch et al. |
| 6,367,488 | B1 | 4/2002 | Murch et al. |
| 6,455,086 | B1 | 9/2002 | Trinh et al. |
| 6,557,568 | B1 | 5/2003 | Murch et al. |
| 6,662,813 | B1 | 12/2003 | Murch et al. |
| 6,773,737 | B1 | 8/2004 | Roselle et al. |
| 6,808,729 | B1 | 10/2004 | Roselle et al. |
| 6,831,050 | B2 | 12/2004 | Murch et al. |
| 6,867,233 | B2 | 3/2005 | Roselle et al. |
| 7,314,857 | B2 | 1/2008 | Madhyastha |
| 2001/0046979 | A1 | 11/2001 | Roselle et al. |
| 2006/0241182 | A1 | 10/2006 | Jun et al. |
| 2006/0276541 | A1 | 12/2006 | Tautvydas et al. |
| 2007/0048344 | A1 | 3/2007 | Yahiaoui et al. |
| 2008/0045592 | A1 | 2/2008 | Broadbent et al. |
| 2008/0057135 | A1 | 3/2008 | Allen et al. |
| 2008/0250710 | A1 | 10/2008 | Hirasawa et al. |
| 2008/0264858 | A1 | 10/2008 | Stamets |
| 2009/0074971 | A1 | 3/2009 | McMahon et al. |

FOREIGN PATENT DOCUMENTS

| | | |
|---|---|---|
| JP | 07138139 | 5/1995 |
| WO | 02056694 | 7/2002 |
| WO | 2008126374 A1 | 10/2008 |

OTHER PUBLICATIONS

Zhao et al. ("Inactivation of *Salmonella* and *Escherichia coli* O157:H7 on Lettuce and Poultry Skin by Combinations of Levulinic Acid and Sodium Dodecyl Sulfate" Journal of Food Protection, May 2009, 72(5), 928-936).*

Wareing et al. (Microbiology of Soft Drinks and Fruit Juices, in Chemistry and Technology of Soft Drinks and Fruit Juices, Second Edition, 2007 (ed P. R. Ashurst), Blackwell Publishing Ltd, Oxford, UK. p. 279-297).*

(Continued)

*Primary Examiner* — Kortney L Klinkel

(74) *Attorney, Agent, or Firm* — Thomas|Horstemeyer, LLP

(57) ABSTRACT

Antimicrobial compositions are provided comprising a pharmaceutically acceptable organic acid and a pharmaceutically acceptable surfactant. This synergistic combination allows compositions to be formulated at low concentrations that have efficacy in reducing bacterial counts by greater than 3 log within 5 minutes of contact while preserving the organoleptic properties of treated foods, including fresh produce. Also provided are methods for the use of the compositions to reduce the microbial load on the surfaces of foodstuffs, processed food products, and the hard surfaces of food preparation machinery, tools, benches, and the like.

15 Claims, 9 Drawing Sheets

(56) References Cited

OTHER PUBLICATIONS

Leriche, et al., "Behavior of L. monocytogenes in a artificially made biofilm of a nisin-producing strain of *Lactococcus lactis*", International Journal of Food Microbiology, 51(2): 169-182 (1999).
Jeong, et al., "Growth of Listeria monocytogenes at 21 degrees C in biofilms with microorganisms isolated from meat and dairy processing environments", Lebensmittel-Wissenschaft and Technologie, 27(5): 415-424 (1994).
Lasagno, et al., "Selection of bacteriocin producer strains of lactic acid bacteria from a dairy environment", The New Microbiologica : Official Journal of the Italian Society for Medical, Odontoiatric, and Clinical Microbiology, 25(1) 37-44 (2002).
Sulzer, et al., "Growth inhibition of Listeria spp. on Camembert cheese by bacteria producing inhibitory substances", International Journal of Food Microbiology, 14(3): 287-296 (1991).
Jeong, et al., "Growth of Listeria monocytogenes at 10 degrees C in biofilms with microorganisms insolated from meat and dairy processing environments", Journal of Food Protection, 57(7): 576-586(1994).
Beuchat, L. R., et al., "Standardization of a method to determine the efficacy of sanitizers in inactivating human pathogenic microorganisms on raw fruits and vegetables", J. Food. Prot. 64:1079-1084 (2001).
Luo, Y., et al., "Determination of free chlorine concentrations needed to prevent *Escherichia coli* O157:H7 cross-contamination during fresh-cut produce wash", J. Food Prot. 74:352-358 (2011).
Truong, V. T.,et al, "Effect of α-cyclodextrin-cinnamic acid inclusion complexes on populations of *Escherichia coli* O157:H7 and *Salmonella enterica* in fruit juices", J. Food Prot. 73: 92-96 ( 2010).
Venkitanarayanan K., et al., "Inactivation of *Escherichia coli* O157:H7 by combinations of GRAS chemicals and temperature", Food Microbiol. 16:75-82 (1999).
Whitney B. M., et al., "High pressures in combination with antimicrobials to reduce *Escherichia coli* O157:H7 and *Salmonella agona* in apple juice and orange juice", J. Food Prot. 71: 820-824 (2008).
Zhao, T., et al., "Fate of *Escherichia coli* O157:H7 in apple cider with and without food preservatives", Appl. Environ. Microbiol, 59:2526-2530 (1993).
Zhao, T., et al., "Health relevance of the presence of fecal coliforms in iced tea and leaf tea", J. Food Prot, 60:215-218 (1997).
Zhou, F., et al., "Synergistic effect of thymol and carvacrol combined with chelators and organic acids against *Salmonella typhimurium*", J. Food Prot. 70:1704-1709 (2007).
Al Kataoka, et al., "Inactivation of Shiga Toxin-Producing *Escherichia coli* in Single-Strength Lemon and Lime Juices Containing Preservatives", Journal of Food Protection, vol. 74, No. 10; 1746-1750 (2011).
Lejeune J.T., et al., "Livestock Drinking Water Microbiology and the Factors Influencing the Quality of Drinking Water Offered to Cattle", American Dairy Science Association (2001).
Zhao, T., et al., "Influence of freezing and freezing plus acidic calcium sulfate and lactic acid addition on thermal inactivation of *Escherichia coli* O157:H7 in ground beef", Journal of Food Protection (2004).
Annamalai, T., et al., "In vitro inactivation of *Escherichia coli* O157:H7 in bovine rumen fluid by caprylic acid", Journal of Food Protection (2004).
Liu X., et al. Experimental Observation on Factors Influencing#C Efficiency of Chlorine Dioxide#C in Killing Enterohemorrhagic *Escherichia coli* O157:H7, Feb. 16, 2007, English abstract only considered.
Robert T. Marshall, "Acids, Pathogens, Foods and Us", Food Protection Trends, vol. 23, No. 11, p. 882-886, 2003.

* cited by examiner

ANTIMICROBIAL COMPOSITION AND USE AS FOOD TREATMENT

CROSS REFERENCE TO RELATED APPLICATION

This application is a Continuation-in-Part of U.S. non-provisional application Ser. No. 12/811,560, entitled "ANTIMICROBIAL COMPOSITION AND USE" filed Jul. 2, 2010, now abandoned which claims priority from PCT application entitled "Antimicrobial Composition and Use," having serial number PCT/U.S.2009/44815, filed on May 21, 2009. This application also claims priority and benefit under 35 USC §119(e) to U.S. Provisional Patent Application Ser. Nos. 61/055,299 filed on May 22, 2008, 61/085,050 filed Jul. 31, 2008, and 61/151,377, filed Feb. 10, 2009, and to U.S. Provisional Patent Application Ser. No. 61/446,082 filed on Feb. 24, 2011, the disclosures of which are incorporated herein by reference in their entireties.

TECHNICAL FIELD

The present disclosure is generally related to methods of use of microbicide compositions for reducing a microbial load of consumable food stuffs. The present disclosure particularly relates to methods of use of microbicide compositions for reducing a microbial load of a raw meat, a vegetable foodstuff, or processed products thereof.

BACKGROUND

Microbial contamination of the food supply, both of solid foods and consumable liquids, is a significant and universal problem in all societies and countries, even those widely assumed to generally provide "safe" food supplies. Contamination may occur at any point in the food supply line, from the source of the foodstuffs, introduced during gathering, transportation and marketing, at the point of food processing, and during storage prior to its consumption. Even with a beverage as simple as water, microbial contamination, and hence potential sources of disease, are readily found or introduced. There is a constant need, therefore, for effective means of reducing to acceptable levels (i.e. levels that do not have pathological effects on humans or animals consuming the foods or liquids) microbial contaminants and which do not initiate changes in the foodstuffs that render them unpalatable and/or unmarketable. Desirable antimicrobials, therefore, must be safe for human and animal consumption, cheap since they can be used to treat enormous amounts of consumable products, preferably of long-lasting in effectiveness, and effective in reducing the viability of a wide-range of possible contaminants.

*Escherichia coli* O157:H7 and *Salmonella* are major causes of severe food borne disease in the United States and continue to be of public health significance. *Salmonella* is one of the most frequent causes of food borne illnesses worldwide. In the United States, it causes an estimated 1.4 million cases of illness, approximately 20,000 hospitalizations, and more than 500 deaths annually (Mead, et al., 1999). FoodNet surveillance data of food borne illnesses revealed that the overall incidence of salmonellosis decreased by only 8% from 1996 to 2004 and incidents of *Salmonella enteritidis* infections has stayed at approximately the same level.

Other pathogens such as, for instance, *Klebsiella, V. cholera, Proteus hauseri, Shigella, Yersinia pestis* and *B. anthracis*, and protozoan, together with the more prominent *E. coli* and *Salmonella*, comprise a wide-spectrum of food-borne and water-borne pathogens that threaten the safety of the food supply and are now considered a matter of homeland security relevance. These food-borne and water-borne microorganisms are also associated with the spoilage of beverages such as fruit juices, and other protein and/or sugar-containing beverages. Therefore, the development of a unique, pluripotent, widely applicable, and easy to manufacture countermeasure is desirable.

Many pathogen reduction interventions in the meat and poultry industry involve the use of acids or antimicrobial chemical treatments, but most of these interventions reduce *E. coli* O157:H7 or *Salmonella* contamination by only 10- to 100-fold. There were in 2007 22 recalls of ground beef contaminated with *E. coli* O157:H7, indicating there are ongoing needs for more effective antimicrobial interventions in the meat industry.

SUMMARY

Aspects of the present disclosure, therefore, encompass embodiments of a method of reducing a microbial population on the surface of a foodstuff, where the method can comprise the step of contacting the foodstuff with an antimicrobial composition, the antimicrobial composition comprising a monoprotic organic acid having a carbon backbone of 4 to 10 carbons, an anionic surfactant, and a solvent, for a time effective in reducing the viability or the cell density of the microbial population on the surface of a foodstuff.

In embodiments of this aspect of the disclosure, the monoprotic organic acid can have the general structure of:

I

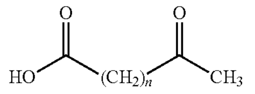

wherein n is an integer from 1 to 6, the total concentration of the monoprotic organic acid can be about 0.1% to about 20% by weight per volume of the antimicrobial composition, and the anionic surfactant can be about 0.1 to 10% by weight per volume of the antimicrobial composition.

In embodiments of this aspect of the disclosure, the monoprotic organic acid can be levulinic acid.

In embodiments of this aspect of the disclosure, the surfactant can be selected from the group consisting of: sodium dodecyl sulfate, sodium laureth sulfate, a quaternary ammonium cation, cetyl pyridinium chloride, and benzalkonium chloride.

In some embodiments of this aspect of the disclosure, the surfactant is sodium dodecyl sulfate.

In some embodiments of this aspect of the disclosure, the monoprotic organic acid can be levulinic acid and the surfactant is sodium dodecyl sulfate.

In embodiments of this aspect of the disclosure, the composition can comprise about 0.3 to about 3% levulinic acid by weight per volume of the antimicrobial composition, and about 0.05% to about 2% sodium dodecyl sulfate by weight per volume of the antimicrobial composition.

In embodiments of this aspect of the disclosure, the antimicrobial composition can be delivered to the foodstuff as a wash, a spray, or a foam.

In embodiments of this aspect of the disclosure, the foodstuff can be a raw foodstuff, a cooked foodstuff, a processed foodstuff, a packaged foodstuff, or any combination thereof.

In embodiments of this aspect of the disclosure, the foodstuff can comprise (i) a plant, a part thereof, a vegetable product, a processed plant product, or any combination thereof, and (ii) a whole animal, an animal carcass, a part thereof, an animal product, milk, an egg, a processed animal product, or any combination thereof.

In embodiments of this aspect of the disclosure, the foodstuff can be a plant, a part thereof, a vegetable product, a processed plant product, or any combination thereof. In these embodiments of this aspect of the disclosure, the foodstuff can be a leaf, a stem, a flower, a seed, a nut, a fruit, a tuber, a root, or any combination thereof.

In embodiments of this aspect of the disclosure, the foodstuff can be a whole animal, an animal carcass, a part thereof, an animal product, milk, an egg, a processed animal product, or any combination thereof.

In embodiments of this aspect of the disclosure, the method can provide a processed foodstuff with antibacterial qualities, said method comprising combining the antimicrobial composition with a raw food material to form a mixture; and processing said mixture to form a processed foodstuff.

In embodiments of this aspect of the disclosure, the raw food material can be an unprocessed meat, and said mixture is then ground.

In embodiments of this aspect of the disclosure, the raw food material can be shelved nuts to form a mixture, and said mixture is then ground for the preparation of a nut butter.

In embodiments of this aspect of the disclosure, the antimicrobial composition can be added to a package with a foodstuff.

BRIEF DESCRIPTION OF THE DRAWINGS

Further aspects of the present disclosure will be more readily appreciated upon review of the detailed description of its various embodiments, described below, when taken in conjunction with the accompanying drawings.

Period of exposure: FIG. 1A, 0 min; FIG. 1B, 10 min; FIG. 1C, 45 min; FIG. 1D, 90 min; FIG. 1E, 180 min.

Period of exposure: FIG. 2A, 0 hr; FIG. 2B, 1 hr; FIG. 2C, 2 hrs; FIG. 2D, 3 hrs; FIG. 2E, 4 hrs.

Period of exposure: FIG. 3A, 0 hr; FIG. 3B, 1 hr; FIG. 3C, 2 hrs; FIG. 3D, 3 hrs; FIG. 3E, 4 hrs.

DESCRIPTION

Figure 1A:
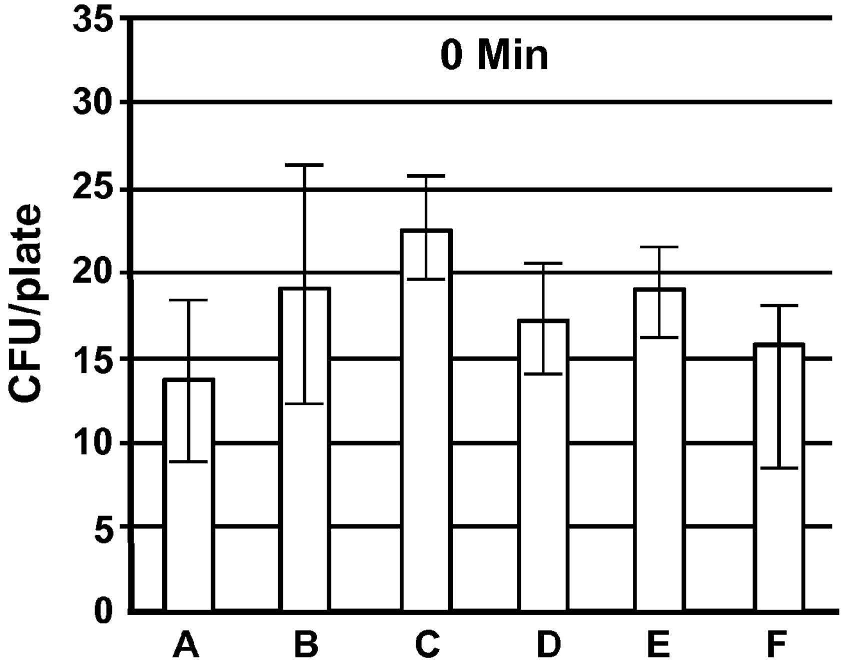
FIGS. 1A-1E illustrate bar graphs demonstrating the efficacy of levulinic acid and SDS, alone or in combination, to kill spores of *Bacillus anthracis* Sterne. Spores were exposed to one of six different solutions: A: 3% levulinic acid plus 2% SDS; B: 2% levulinic acid plus 1% SDS; C: 0.5% levulinic acid plus 0.05% SDS; D: 3% levulinic acid; E: 2% SDS; or F: water (serving as the control) for various lengths of time before testing the spores for viability relative to the control sample. Average plate counts are based on counting three plates; error bars indicate+/−one standard deviation.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing and claiming the disclosure, the following terminology will be used in accordance with the definitions set forth below.

The terms "microorganism" or "microbe" as used herein are intended to include living cellular organisms, both unicellular and multicellular that are less than 5 mm in length, and include but are not limited to bacteria, fungi, archaea, protists; green algae, plankton, planarian, amoebas and yeasts, or spores formed by any of these.

The term "antimicrobial" as used herein refers to a compound that exhibits microbicide or microbiostatic properties that enables the compound to kill, destroy, inactivate, or neutralize a microorganism; or to prevent or reduce the growth, ability to survive, or propagation of a microorganism.

The term "acid" as used herein refers to any chemical compound that, when dissolved in water, gives a solution with a hydrogen ion activity greater than in pure water, i.e. a pH less than 7.0. An "organic acid" is a carbon containing compound (except for carbonic acid) with acidic properties. The term "organic acid" refers to a compound having a hydrocarbon chain and an acid group covalently bound to the hydrocarbon chain. The hydrocarbon chain can be of any length and can be a straight chain or a branched chain, preferably of 1-10 carbon atoms. The most common organic acids are the carboxylic acids whose acidity is associated with their carboxyl group —COOH. However, additional compounds that lack a carboxylic function group can still function as an acid in accordance with the present disclosure if the compound ionizes in aqueous solution to yield hydrogen ions. Accordingly, eugenol is considered an acid within the context of the present disclosure due to the electron withdrawing properties of the phenol ring on the hydroxyl group subsitutent. Sulfonic acids, containing the group $OSO_3H$, are another typical, but relatively stronger group of organic acids. The organic acids used in the present disclosure may also include additional functional groups extending from the hydrocarbon backbone. The carbon chain of the organic acid can further be functionalized by a hydroxyl, a carbonyl, an amino, an alkylamino, a sulfonyl, or a thiol group. A monoprotic acid is an acid that is able to donate one proton per molecule during ionization.

The term "surfactant" as used herein refers to a surface active agent that modifies interfacial tension of water. Typically, surfactants have one lipophilic and one hydrophilic group in the molecule. Broadly, the group includes soaps, detergents, emulsifiers, dispersing and wetting agents, and several groups of antiseptics. More specifically, surfactants include stearyltriethanolamine, sodium dodecyl sulfate, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose. The surfactant used in the compositions of the present disclosure may be selected from any of the known organic surfactants (i.e., organic compounds that are amphiphilic, containing both hydrophobic groups and hydrophilic groups), including, ionic (cationic or anionic) and nonionic surfactants, or mixtures thereof. The surfactant can be an ionic surfactant, and more typically an anionic surfactant and have from about 10 to about 20 length carbon chain linked to the hydrophilic head group. The surfactant can be an organic phosphate or sulfate wherein the carbon chain of said organic phosphate or sulfate can comprises at least about 8 carbon atoms.

The term "pharmaceutically acceptable" as used herein refers to any compound that can be safely administered to warm blooded vertebrates including humans, or included in foods consumed by animals or humans. Pharmaceutically acceptable acids and surfactants include acids and surfactants that are classified by the United States Food and Drug Administration (FDA) as being Generally Regarded As Safe (GRAS), and encompass any of the agents approved by a regulatory agency of the US Federal government or listed in the US Pharmacopeia for use in animals, including humans.

A quaternary ammonium cation is a compound of the general structure:

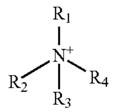

or

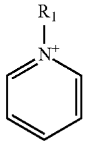

wherein $R_1$, $R_2$, $R_3$, and $R_4$ are independently selected from the group consisting of $C_1$-$C_{20}$ alkyl and salts thereof.

As used herein the term “benzalkonium chloride” refers to a single alkylbenzyldimethylammonium chloride of the general structure

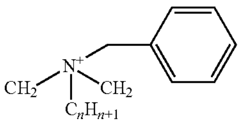

wherein n is an integer selected from the group consisting of 6, 8, 10, 12, 14, 16, 18 and 20, or mixtures of two or more such compounds.

As used herein an “effective” amount of an anti-microbial composition refers to a concentration of active agent that provides the desired effect, i.e., a log order reduction in the microbial count in a liquid, on a surface of a foodstuff, or on a hard surface without reducing organoleptic properties of the food substance.

As used herein the term “germination” refers to the initiation of growth of an embryonic plant contained within a seed, through completion of establishment of the seedling, wherein the seedling has exhausted the food reserves stored in the seed.

As used herein “organoleptic properties” relating to properties that can be detected by human or animal senses (taste, color, odor, feel) unaided by mechanical and analytical devices.

As used herein a “food substance” relates to any material that is edible by mammals, including for example, a human. The term “foodstuff” as used herein includes both solid and liquid ingestible materials for man or animals, which materials usually do, but need not, have nutritional value. Thus, foodstuffs include food products, such as, meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like. The term “processed foodstuff” as used herein refers to a food substance or foodstuff that has been altered from its state before or immediately after harvesting to a state that is intended for storage, consumption, marketing and the like and wherein the foodstuff has been transformed from its native state of form, color, texture, taste, chemical content and the like, including mechanical or thermal (cooking) transformation, combining with other foodstuffs, and the like.

The terms “plant”, “vegetable product”, “processed plant product” as used herein refer to any vegetable, cultivated or gathered, that is harvested for animal or human consumption, or a part thereof, including seeds, grains, cereals, nuts, fruits, leaves, roots, tubers, and the like. The terms “whole animal”, “animal carcass”, “animal product” as used herein refer to an animal, wild or domesticated that can be slaughtered for human or animal consumption, including, but not limited to, cow, horse, goat, sheep, pig, poultry, fish, shell-fish, and the like, a dead animal or a dressed and butchered carcass, or butchered pieces of said slaughtered animal, milk, eggs, skin, and the like. The term “processed animal product” includes any animal derived tissue, including muscle (meat) or organ that is removed from a carcass, cooked, sliced, minced, ground, alone, or in combination with other meat or vegetable substances, preservatives, flavorings, colorants, and the like.

The term “cylinder foam test” as used herein refers to a test for measuring both the foamability of compositions and the persistence of the foamed state. In general, the test comprises the steps of placing a test composition into a stoppered, graduated cylinder so that the composition occupies a predetermined height of the cylinder (e.g., about ⅓ to about ½ of the height of the stoppered, graduated cylinder). The stoppered, graduated cylinder is then inverted approximately 10 times to generate a foam. The height of foam is measured immediately after the inverting step as a measure of the foamability of the composition. The foamed composition is then left undisturbed to determine the foam half-life (time required for the foam to lose half its height in the graduated cylinder). The cylinder foam test is conducted at room temperature under 1 standard atmosphere pressure (i.e., 101.3 kPa (about 760.01 mm Hg) or 29.92 in Hg).

The term “food processing surface” as used herein refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing, blancher cleaning, food packaging materials, cutting boards, beverage chillers and warmers, meat chilling or scalding equipment, cooling towers, food processing garment areas (including drains).

DESCRIPTION

The present disclosure encompasses antimicrobial compositions suitable for application to a wide spectrum of foodstuffs, and sufficiently benign as not to result in changes to the treated foods that would render them unfit for marketing or consumption. The compositions of the disclosure comprise combinations of surfactants that with a plurality of acids produce a synergistic effect in relation to the antimicrobial effectiveness of the individual compounds. This surprising synergy allows the formulation of compositions wherein the active agents (comprising an acid and a surfactant) are present at concentrations effective to reduce bacterial counts on the surface of food substances by a factor between about $10^3$ and about $10^8$ without altering the organoleptic properties of the treated food substance. The active agents include acids and surfactants that are FDA-approved food additives, and the treated food substances are selected from poultry, eggs, fish, seafood, meat or fresh produce.

The present disclosure, therefore, provides a composition comprising a pharmaceutically acceptable acid and a pharmaceutically acceptable surfactant, wherein the maximum concentration of total acid present in the composition is about 0.05 to about 10% by weight per volume in water (0.5-100 grams/L) and the maximum concentration of total surfactant is about 0.5% to about 2% by weight per volume in water (5-20 grams/L), or the maximum concentration of total acid present in the composition is about 0.05 to about 5% by weight per volume in water (0.5-50 grams/L) and the maximum concentration of total surfactant is about 0.5% to about 1% by weight per volume in water (5-10 grams/L), or the maximum concentration of total acid present in the composition is about 0.05 to about 5% by weight per volume in water (0.5-50 grams/L) and the maximum concentration of total surfactant is about 0.5% to about 2% by weight per volume in water (5-20 grams/L).

The pharmaceutically acceptable acid is an acid that has been classified by the US Department of Agriculture as being Generally Regarded As Safe (GRAS) and includes, but is not limited to, levulinic acid, caprylic acid, caproic acid, citric acid, eugenol, adipic acid, tartaric acid, fumaric acid, lactic acid, phosphoric acid, hydrochloric acid, succinic acid, malic acid, and sorbic acid.

The pharmaceutically acceptable surfactant can be selected from any ionic (cationic or anionic) or non-ionic surfactants that are compatible for human use. The surfactant, therefore, can be a functionalized organic acid having a hydrocarbon chain length of 2 to 20 carbons, wherein the functionalizing group is selected from hydroxyl, amino, carbonyl, sulphonyl, phosphate and thiol groups. Such surfactants are known to those skilled in the art in the field of food industry and include, for example, sodium dodecyl sulfate (SDS), sodium laureth sulfate (SLS; or sodium lauryl ether sulfate, SLES), cetyl pyridinium chloride (CPC), cocamide MEA (MEA), cocamide DEA (DEA), benzalkonium chloride, and ethylenediamine tetraacetic acid ($H_4EDTA$) and its salts such as $Na_4EDTA$ and $Na_2H_2EDTA$. The surfactants used may also include side group substituents attached to the hydrocarbon backbone. Such substituents can be selected from $H_2PO_3$, $C_1$-$C_8$ hydroxylalkyl and $C_5$-$C_6$ aryl hydroxyl, mono-, di-, tri- and tetra-alkylammonium halides, sulfates and phosphates, wherein at least one of the alkyl substituents of the alkylammonium halide comprises at least 10 carbon atoms and more typically 10-25 carbon atoms.

The acid selected for use in the present disclosure has the general structure of Formula I:

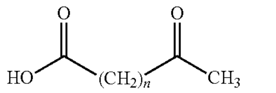

I wherein n is an integer selected from 1 to 10. For example, the acid can have the structure of formula I wherein n is from 1 to 3, such as levulinic acid. Levulinic acid, in the compositions of the disclosure, has been found to have superior qualities relative to other organic acids with regards to it ability, when used in conjunction with low concentrations of a surfactant (e.g., about 0.05% to about 2.0% w/v), to reduce viable microbe concentrations on a food by greater than 2 log within 5 minutes of exposure. The surfactant can be, but is not limited to, sodium dodecyl sulfate (SDS), sodium laureth sulfate (SLS; or sodium lauryl ether sulfate, SLES), cetyl pyridinium chloride (CPC), cocamide MEA (MEA), cocamide DEA (DEA), benzalkonium chloride and ethylenediamine tetraacetic acid ($H_4EDTA$) and most advantageously can be sodium dodecyl sulfate (SDS). Furthermore, the antimicrobial activity of the present compositions is accomplished without producing any detectable impact (by unaided human senses) on the organoleptic properties of the treated food.

The present disclosure, therefore, provides an antimicrobial composition comprising levulinic acid and a surfactant, wherein the concentration of the levulinic acid is about 0.5% to less than 5% (w/v) and the concentration of the surfactant is about 0.05% to 2% (w/v). This combination, including for example levulinic acid and SDS, has been found to be particularly efficacious as an antimicrobial composition that simultaneously preserves the organoleptic properties of a treated food substance. This specific combination has been shown to be several orders of magnitude superior and/or faster in its ability to kill pathogens, than other acid/surfactant combinations. The antimicrobial compositions disclosed herein are formulated at an acid pH, including for example a pH ranging from 2.5 to 3.5, and more typically a pH of 3.0 to 3.2.

The combination of a pharmaceutically acceptable acid and a surfactant have been found to exhibit a synergistic high antimicrobial activity, thus allowing for the use of low concentrations of the active agents to obtain rapid killing of large numbers of microbes upon contact. Accordingly, the low concentration compositions disclosed herein have surprising activity in reducing microbial populations on the surfaces of food items (by several log factors upon contact) without impacting the organoleptic properties of the food item. A method of treating a food substance to reduce resident populations of microbial and/or bacterial populations is provided. The method comprises the steps of contacting the surfaces of the food substance with a composition comprising a pharmaceutically acceptable acid and a pharmaceutically acceptable surfactant, wherein the maximum concentration of total acid present in the composition is about 0.3 to about 3% by weight per volume in water (3-30 grams/L) and the maximum concentration of total surfactant is about 0.01% to about 1% by weight per volume in water (0.1-10 grams/L). The antimicrobial compositions disclosed herein can be formed as a foam and the surface to be treated is contacted with the foamed composition. The method can be used to reduce resident populations of foodborne microorganisms including, but not limited to, *E. coli, Salmonella, Listeria, C. botulinium, C. perfringens, C. jejuni, Giardia lamblia, C. parvum, Staphylococcus aureus, Aspergillus flavus, B. anthracis, B. cereus* and *Y. pestis*.

The levulinic acid plus SDS treatment disclosed herein can greatly reduce by >5 log CFU/g *E. coli* O157:H7 and *Salmonella* contamination of produce and poultry and may also be useful for beef. In addition the shelf life of treated meat may be extended because of reduction of spoilage bacteria. Levulinic acid was selected as the primary focus of this study because it can be produced at low cost and in high yield from renewable feedstocks. Its safety for human application through respiratory absorption has been widely tested and it has GRAS status for direct addition to food as a favoring substance or adjunct (24, FDA 2008, 21 CFR, 172.515). Sodium dodecyl sulfate has GRAS status for multipurpose additives (25, FDA 2007, 21 CFR, 172.822). It is approved for use in a variety of foods, including egg whites, fruit juices, vegetable oils, and gelatin as a whipping or as a wetting agent.

It is contemplated, however, that the compositions and methods of the disclosure may be applied to a foodstuff desired to be treated by application as a wash, a spray, a foam, or by any other suitable means that will allow the surface of the foodstuff to be exposed to the antimicrobial composition. The compositions of the disclosure are also suitable for mixing with a foodstuff during a manufacturing procedure such as meat grinding, pureeing, packaging, and the like, and are also suitable for inclusion with the finished product in a package or other container. In particular, the antimicrobial compositions herein disclosed are especially advantageous for the treatment of ground meat that has proven particularly susceptible to microbial contamination during preparation.

Any foodstuff may be considered suitable for treatment with the compositions and methods herein disclosed. Besides animal carcasses, meat and organs derived therefrom may be treated, and the antimicrobial efficacy has been demonstrated, even in the presence of high levels of organic contamination such as feces, a major source of microbes. Plant material, including whole plants, leaves, stems, etc. seeds, fruits, and the like may also be decontaminated using the compositions and methods of the disclosure.

In one embodiment of the methods of the disclosure is decontamination and treatment of seeds. The method comprises the step of contacting the seeds with a composition comprising levulinic acid and a surfactant. In one specific embodiment, the levulinic acid compositions of the present disclosure are used to treat seeds (including prophylactic treatments) to eliminate acidovorax, including for example the treatment of cucurbitaceas (e.g., watermelon) as well as in grains. In another embodiment, a method of inhibiting the growth of microbes during seed germination is provided. In this method, seeds are contacted prior to, and during the germination of the seeds with a composition comprising levulinic acid and a surfactant. Surprisingly, a composition comprising about 0.3 to about 5% (w/v) levulinic acid, and 0.01 to about 3% of a surfactant has been found to be an effective antimicrobial composition that does not substantially impact seed viability or germination rates.

The antimicrobial compositions provided herein, therefore, comprise a pharmaceutically acceptable acid and a pharmaceutically acceptable surfactant. Surprisingly, the compositions disclosed herein are capable of reducing a microbial population of a liquid or a surface in contact with a microorganism by a factor greater than $10^2$, including by a factor of $10^3$ to a factor of $10^8$, using a combination of an acid and surfactant at concentrations that are otherwise ineffective when used separatedly. The individual active ingredients of the present compositions are ineffective in reducing microbial cell count by a factor greater than $10^2$, even when the active agents are used separately at 2× or 5× the effective concentration used in the combination.

The concentration of the pharmaceutically acceptable acid in the antimicrobial compositions of the disclosure can be within the range of about 0.03% to about 20%, and advantageously about 0.03% to about 3%, or about 0.05% to about 2%, or about 0.05% to about 1%, or about 0.1% to about 3%, or about 0.3% to about 3%, or about 0.3% to about 2%, or about 0.5% to about 3%, or about 0.5% to about 2%, or about 0.5% to about 1%, weight per volume in water. The concentration of the pharmaceutically acceptable surfactant in the antimicrobial compositions of the disclosure is within the range of about 0.005% to about 10%, and advantageously about 0.005% to about 3%, or about 0.01% to about 3%, or about 0.05% to about 3%, or about 0.1% to about 2%, or about 0.05% to about 2%, or about 0.5% to about 2% by weight per volume in water.

The antimicrobial compositions herein provided comprise a linear monoprotic organic acid and an ionic long chain ($C_8$-$C_{30}$) surfactant. The organic acid can be a linear monoprotic organic acid comprising a carbon backbone of 4 to 10 carbons. In some embodiments of the antimicrobial compositions of the disclosure, the general structure of the acid can be $CH_3(CH_2)_mCOOH$, with m being an integer selected from 2-8, and the surfactant can be, but is not limited to, sodium dodecyl sulfate (SDS), sodium laureth sulfate (SLS; or sodium lauryl ether sulfate, SLES), cetyl pyridinium chloride (CPC) or benzalkonium chloride. In some embodiments, therefore, the composition can comprise an acid of the general structure $CH_3(CH_2)_mCOOH$, with m being an integer selected from 2-8 and the surfactant is sodium dodecyl sulfate (SDS) or sodium laureth sulfate (SLS; or sodium lauryl ether sulfate, SLES). In another embodiment the composition comprises an acid of the general structure $CH_3(CH_2)_mCOOH$, or

I

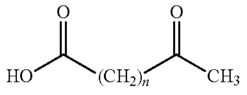

wherein m is an integer selected from 2-8 and n is an integer selected from 1 to 10. The surfactant can be, but is not limited to, a cation of the general structure:

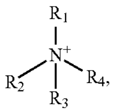,

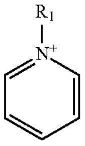

or

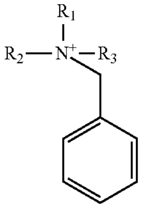

wherein $R_1$, $R_2$, $R_3$, and $R_4$ are independently selected from the group consisting of $C_1$-$C_{20}$ alkyl, and salts thereof. In some embodiments, $R_1$ is $C_6$-$C_{20}$ alkyl and $R_2$, $R_3$, and $R_4$ are independently selected from the group consisting of $C_1$-$C_2$ alkyl.

Various embodiments of antimicrobial compositions of the disclosure can comprise an organic acid such as, but not limited to, eugenol, hexanoic acid, levulinic acid, succinic acid, and the like. For example, one advantageous acid component of the antimicrobial composition consists of an acid having the general structure of Formula I:

I

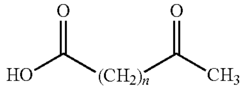

where n is an integer selected from 1 to 10. In some embodiments, the acid can have the structure of formula I where n is an integer selected from 1 to 3.

The surfactant can be, but is not limited to, benzalkonium halide, cetylpyridinium chloride, cetylpyridinium bromine, and SDS and the antimicrobial composition can comprise, but is not limited to, such as 0.05% to 2.0% (w/v) eugenol plus 0.05% to 1.0% (w/v) SDS; 0.05% to 2.0% (w/v) hexanoic acid plus 0.05% to 1.0% (w/v) SDS; 0.05% to 2.0% (w/v) levulinic acid plus 0.05% to 1.0% (w/v) benzalkonium chloride; 0.05% to 2.0% (w/v) levulinic acid plus 0.05% to 1.0% (w/v) cetylpyridinium chloride; or 0.05% to 1.0% (w/v) succinic acid plus 0.05% to 2.0% (w/v) SDS; 0.5% eugenol plus 0.05% SDS (pH 3.2); 0.5% hexanoic acid plus 0.05% SDS (pH 3.2); 0.5% levulinic acid plus 0.05% benzalkonium chloride (pH 3.1); 0.5% levulinic acid plus 0.05% cetylpyridinium chloride (pH 3.1); or 0.5% succinic acid plus 0.05% SDS (pH 2.9); or combinations thereof.

Previous studies revealed that combinations of different organic acids can be used as anti-bacterial agents based on their killing effects on *E. coli* O157:H7 and *Campylobacter* (Zhao, et al. 2006). Levulinic acid is an organic acid that can be produced cost effectively and in high yield from renewable feedstocks (Bozell, et al. 2000, Fang & Hanna, 2002). Its safety for humans has been widely tested and FDA has given it GRAS status for direct addition to food as a flavoring agent or adjunct (21 CFR, 172.515). As disclosed herein, the antimicrobial effect of 1% by weight levulinic acid alone will not suffice to kill more than 1 log colony-forming unit (CFU) *Salmonella*/ml within 30 mins, and its bactericidal effect was increased only to 3.4 log CFU/ml within 30 mins when its concentration was increased to 3% by weight, as shown, for example, in Tables 1-3.

Sodium dodecyl sulfate (SDS) also has GRAS status (21 CFR, 172.210) and can be found, for example as 0.5% wt of gelatin, as a whipping agent used in marshmallows, and at 0.0125% in liquid and frozen egg whites. It has been widely studied and is used as a surfactant in household products such as toothpastes, shampoos, shaving foams, and bubble baths. The SDS molecule has a tail of 12 carbon atoms attached to a sulfate group, giving the molecule the amphiphilic properties required of a surfactant. As also disclosed herein, SDS by itself has very little antimicrobial effect.

As reported herein, combining a pharmaceutically acceptable surfactant with a pharmaceutically acceptable acid synergistically enhances the antimicrobial activity of the respective surfactant and acid. SDS when combined with organic acids dramatically increased the bactericidal effect of organic acid treatments. The substantial bactericidal effect of a combination of levulinic acid and SDS on *E. coli* O157:H7 and *Salmonella* was validated on fresh produce (both animal and plant in origin, poultry wings, chicken skin and water containing different levels of organic contamination including fecal matter and feathers, as shown, for example, in Tables 4-8. The bactericidal activity of this combination of chemicals remained effective even in an organic-rich environment containing fecal matter or feathers, representative of the environment of a slaughter house and poultry or meat processing plant.

The antimicrobial compositions disclosed herein can be used to reduce the population of an undesirable microbe on surface, including that of a food substances or food handling equipment that may come into contact with contamination or foodstuffs. Accordingly, the disclosure encompasses methods for contacting an object with a composition comprising levulinic acid and a pharmaceutically acceptable surfactant, in particular sodium dodecyl sulfate. Advantageously, the antimicrobial compositions have been found to remain effective even in an organic-rich environmental containing such as fecal matter. Thus the compositions can be used as a single wash treatment of surfaces that may contain such materials in addition to pathogenic microbes.

An antimicrobial composition comprising levulinic acid and a surfactant is provided wherein the composition is effective in reducing resident microbial populations on food substance. For example, a food contaminated with $10^8$-$10^9$ CFU/ml *E. coli* O157:H7 can be treated with the antimicrobial compositions disclosed herein to reduce the presence of viable bacteria by a factor greater than $10^3$ (including reductions of $10^4$, $10^5$, $10^6$ and $10^7$ or even higher) after exposure to said composition for five minutes, under conditions otherwise favorable to proliferation of said *E. coli* O157:H7. The concentration of said levulinic acid and surfactant are at concentrations that are ineffective in reducing said resident microbial population when used separatedly. The concentration of each of the levulinic acid and surfactant components is at a concentration 0.5×, 0.25×, 0.1×, or less than 0.1×, of the concentration required to produce a significant reduction (e.g., greater than one log reduction within 5 minutes) in an *E. coli* O157:H7 microbial population when the respective component (i.e., levulinic acid or surfactant) is used separately. The concentration of the levulinic acid in the compositions of the present disclosure is no more than about 20% to about 0.5% (w/v), about 10% to about 0.5% (w/v), about 5% to about 0.5% (w/v), about 3% to about 0.5% (w/v), about 2.5% to about 0.5% (w/v), about 2.0% to about 0.5% (w/v), about 1.5% to about 0.5% (w/v), about 1.0% to about 0.5% (w/v), about 0.5% or about 0.25% (w/v). In some embodiments the concentration of the levulinic acid is less than 2.5% (w/v) or less than 2.0% (w/v) and in a further embodiment the concentration of the levulinic acids is about 0.5% (w/v) levulinic acid. These concentrations of levulinic acid in combination with a pharmaceutically acceptable surfactant at concentrations of less than 2% have been found to retain the organoleptic properties of foods, including produce. The concentration of the surfactant in one embodiment of the present compositions is no more than about 0.01% to about 1%, or about 0.01% to about 0.1% and more typically is about 0.05% (w/v).

In one embodiment the surfactant is a sulfate, sulfonate or carboxylate anion and in another embodiment the surfactant is a quaternary ammonium cation. In one embodiment the quaternary ammonium cation is benzalkonium chloride, cetylpyridinium bromide or cetylpyridinium chloride.

A method for the rapid killing of microbial strains, including bacteria, yeasts, and molds, is provided. The method comprises contacting the beverage with a composition comprising a SDS and levulinic acid, wherein the concentration of the organic acid is about 20.0% to about 0.5%, about 10.0% to about 0.5%, about 5.0% to about 0.5%, about 3.0% to about 0.5%, about 2.0% to about 0.5%, about 1.0% to about 0.5% or about 0.5% (w/v) or less, and the concentration of the surfactant is less than about 5% to about 0.05%, about 0.5% to about 0.05%, 0.1% to about 0.05%, or 0.05% (w/v).

The organic acid is selected from the group consisting of lactic acid, acetic acid, and levulinic acid and the surfactant is an anionic surfactant, including for example SDS. The composition can comprise levulinic acid and SDS, and in a further embodiment the composition comprises a maximum concentration of 0.3 to 3% by weight levulinic acid and a maximum concentration of 0.05 to 1% by weight SDS. In one embodiment, the organic acid/SDS compositions disclosed herein are used to inactivate bacterial strains including pathogenic strains of *Salmonella* and *E. coli*. The treatments can be conducted at temperatures favorable to retaining the desirable properties of fresh produce, including at temperatures of 20° C. to 25° C., or 20° C. to 22° C.

The surface to be treated can be contacted with the levulinic acid containing solution by any standard technique, including spraying, washing, immersion, rinsing, soaking (with or without agitation) and similar methods known to those skilled in the art. Advantageously, applicants have found that by spraying the present compositions under relatively low pressure, the composition will be applied as a foam. For example using a composition comprising 2% SDS and a simple weed sprayer, the composition is applied as a foam that is comparable to that when a foaming agent is needed for applying disinfectants to equipment and environmental surfaces in food processing facilities. The foam persists for at least 20 minutes if left undisturbed. In one embodiment the pressure used to produce consistant form (e.g., one that lasts for 20 minutes) for a 3% levulinic acid plus 2% SDS (w/v) is 15 to 35 psi. The concentration of the active agents can be reduced to 2% levulinic acid and 1% SDS and formation of a consistent foam can still be obtained using a similar pressure. The use of a foamed form of the composition is advantageous as it allows for better penetration of the active agents on the treated surface.

When the present composition is provided as a foam, the composition has a cellular structure that can be characterized as having several layers of air cells that provide the composition with a foamy appearance. It should be understood that the characterization of a foam refers to the existence of more than simply a few air bubbles and in one embodiment the foam retains over 20, 30, 40, 50, 60 or 70% of its maximum height in a cylinder foam test 10 minutes after agitation ceases. In one embodiment the foamed antimicrobial composition of the present disclosure retains at least 20% of its height in a cylinder foam test 5 minutes after agitation is ceased.

The cylinder foam test has been used in the surfactant industry to evaluate the foamability of test compositions. In general, the cylinder foam test is conducted by adding a test composition to a stoppered, graduated cylinder so that the composition occupies a predetermined height of the cylinder (e.g., about ⅓ to about ½ of the height of the stoppered, graduated cylinder). The stoppered, graduated cylinder is inverted approximately 10 times and the height of foam generated can be recorded. The persistence of the foam can be determined by measuring the height of the foamed composition in the graduated cylinder over time in the absence of further agitation. The test is typically conducted under room temperature under standard atmospheric conditions.

Typically, the antimicrobial compositions disclosed herein can be formed as a foam using simple mechanical foaming heads known to those skilled ing the art that function by mixing air and the composition to create a foamed composition. However, the use of known chemical foaming mechanisms is also suitable for forming foams in accordance with the present disclosure. For chemical foaming, the antimicrobial composition can include ingredients that create foam as a result of a chemical interaction, either with other ingredients in the composition, or with substances present in the applicable environment. These components can be provided as a 2-part composition that can be combined when foaming is desired.

Foaming can be accomplished, for example, using a foam application device such as a tank foamer or an aspirated wall mounted foamer, e.g., employing a foamer nozzle of a trigger sprayer. For example, foaming can be accomplished by placing the composition in a fifteen gallon foam application pressure vessel, such as a fifteen gallon capacity stainless steel pressure vessel with mix propeller. The foaming composition can then be dispensed through a foaming trigger sprayer. A wall mounted foamer can use air to expel foam from a tank or line.

The antimicrobial compositions disclosed herein can be optionally administered to a food substance or a food processing surface as a foam. The foam can be prepared by mixing air with the antimicrobial composition through use of a foam application device. Mechanical foaming heads that can be used according to the disclosure to provide foam generation include those heads that cause air and the foaming composition to mix and create a foamed composition. That is, the mechanical foaming head causes air and the foaming composition to mix in a mixing chamber and then pass through an opening to create a foam.

Suitable mechanical foaming heads that can be used according to the disclosure include those available from Airspray International, Inc. of Pompano Beach, Fla., and from Zeller Plastik, a division of Crown Cork and Seal Co. Suitable mechanical foaming heads that can be used according to the disclosure are described in, for example, U.S. Pat. No. D-452,822; U.S. Pat. No. D-452,653; U.S. Pat. No. D-456,260; and U.S. Pat. No. 6,053,364. Mechanical foaming heads that can be used according to the disclosure includes those heads that are actuated or intended to be actuated by application of finger pressure to a trigger that causes the foaming composition and air to mix and create a foam. That is, a person's finger pressure can cause the trigger to depress thereby drawing the foaming composition and air into the head and causing the foaming composition and air to mix and create a foam.

Additional foam boosting agents can be added to the antimicrobial compositions to enhance either foamability and/or longevity of the formed foam. The antimicrobial compositions disclosed herein can further comprise a foam boosting solvents selected from the group consisting of glycols, glycol ethers, derivatives of glycol ethers, and mixtures thereof. Suitable glycols include those having at least four carbon atoms such as hexylene glycol.

In one embodiment, a food substance or an object in a food processing environment can be treated with the antimicrobial compositions. A method, therefore, is provided for preparing a processed food with antibacterial qualities. The food is combined with an antimicrobial composition disclosed herein using any standard technique, including for example, spraying, immersion, rinsing, soaking, injecting, washing and the like. Optionally, the food can be more rigorously mixed with the antimicrobial compositions by use of stirring, grinding, pulverizing, macerating, or other known techniques, to produce the combined food and antimicrobial composition. The antimicrobial composition can comprise an organic acid having the general structure of:

I

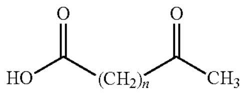

wherein n is an integer selected from 1 to 6, and a surfactant selected from the group consisting of a quaternary ammonium cation, sodium dodecyl sulfate, sodium laureth sulfate, and cetyl pyridinium chloride. Such an antimicrobial composition is combined with a food raw material component to form a mixture. The mixture is then optionally subjected to further processing to form said processed food. In one embodiment the antimicrobial composition component comprises levulinic acid and SDS. In a further embodiment the method comprises combining the antimicrobial composition with unprocessed meats and then grinding the combined components. In another embodiment the food comprises shelved nuts, wherein after combination of the nuts with the antimicrobial composition, the combined components are then ground for the preparation of nut butters. Other foods including fish and seafood can similarly be combined with the presently disclosed antimicrobial compositions. In a further embodiment the antimicrobial compositions disclosed herein can be used as an additive to solutions packaged with a food.

An antimicrobial composition is herein provided comprising an organic acid and an anionic surfactant, wherein the maximum concentration of the acid in the composition is about 0.3 to about 3% by weight per volume in water (3-30 grams/L) and the maximum concentration of total surfactant is about 0.01% to about 1% by weight per volume in water (0.1-10 grams/L). In one embodiment the organic acid is levulinic acid, and the surfactant is sodium dodecyl sulfate (SDS). An antimicrobial composition is provided comprising levulinic acid and a cationic surfactant, wherein the maximum concentration of the acid in the composition is about 0.3 to about 3% by weight per volume in water (3-30 grams/L) and the maximum concentration of total surfactant is about 0.01% to about 1% by weight per volume in water (0.1-10 grams/L). In one embodiment the compositions comprise further antimicrobial agents known to those skilled in the art. For example the compositions may further comprise one or more antimicrobial agents selected from the group consisting of antibiotics, hydrogen peroxide and alcohols.

As disclosed herein, therefore, a combination of two chemicals, which includes an organic acid (classified as generally recognized as safe by FDA, including lactic acid, acetic acid, levulinic acid, caprylic acid, et al.) and sodium dodecyl sulfate (SDS, the anionic surfactant compound) can be used to kill harmful bacterial present on food substances and/or food processing surfaces. In one embodiment the chemical combination comprises 45 mM levulinic acid and 1.73 mM SDS, which can rapidly (within 8 seconds) kill up to 7 log of pathogens, including *Yersinia pestis, Salmonella enteritidis, S. typhimurium* DT104, *Listeria monocytogenes*, and *Escherichia coli* O157:H7. Levulinic acid (45 mM plus SDS (1.73 mM) reduced *S. Enteritidis, S. Typhimurium* DT104 and *E. coli* O157:H7 in fresh produce (lettuce and spinach) by 5 logs as fast as within 15 seconds. There is no apparent organoleptic difference between fresh produce treated with this chemical solution for up to 60 mins and fresh produce treated with water or without treatment.

Thus, as disclosed herein a group of organic acids, including lactic acid, acetic acid, and levulinic acid, were evaluated individually or in combination with sodium dodecyl sulfate (SDS) to kill *Salmonella*. Results revealed that these chemicals, if used individually at 0.5% by weight for the organic acid or 0.05% by weight for SDS, inactivated ≤2 log CFU/ml within 20 minutes at 21° C. Combining any of these organic acids at 0.5% by weight with 0.05% by weight SDS resulted in the surprising result of >7 log CFU/ml inactivation of *Salmonella* within 10 seconds. Accordingly, as disclosed herein harmful microorganisms (such as *Salmonella* and *E. coli* O157::H7 at $10^8$ CFU/ml) can be killed rapidly by treatment with levulinic acid plus SDS. Combinations of different concentrations of levulinic acid (0.3 to 3% by weight in water) plus SDS (0.05 to 1% by weight in water) were evaluated for killing *E. coli* O157:H7 and *Salmonella* on lettuce and spinach. Results revealed that *E. coli* O157:H7 or *Salmonella* populations on either lettuce or spinach or tomato were reduced by greater than 4 log CFU/g after receiving this treatment for 5 minutes at 21° C.

Additional tests were done on chicken skin contaminated with *Salmonella* and in water containing chicken feathers or feces. Results revealed that *Salmonella* cell numbers on chicken skin were reduced by more than 5 log CFU/$cm^2$ after treatment with as little as 0.5% by weight levulinic acid plus 0.05% by weight SDS for 5 minutes, on poultry wings with 3% by weight levulinic acid plus 2% by weight SDS, and in water containing chicken feathers or feces with 1% by weight levulinic acid plus 0.1% by weight SDS. The use of levulinic acid in combination with SDS as a wash solution is highly desirable because of its surprising efficacy in killing food-borne pathogens, low cost, and environmentally friendly nature.

Processing equipment is commercially available for washing produce (and processing other foods), and applicants have found that the levulinic compositions of the present disclosure (eg. compositions having a concentration up to 3% levulinic acid) is not corrosive to such equipment. In particular, applicants have found that using a large stainless steel seed washing unit provided by a seed supplier, not only was the levulinic acid treatment as effective in killing *E. coli* O157:H7 as the gold standard 20,000 ppm calcium hypochlorite, but it was not corrosive to the equipment and even removed rust on chains within the unit. Thus the levulinic acid composition served to clean the unit like a detergent without the undesirable corrosive effect on equipment that is associated with many sanitizers such as chlorine. Accordingly, one embodiment of the present disclosure is also directed to a method of decontaminating equipment and hard surfaces by contacting such equipment and hard surfaces with the levulinic compositions of the present disclosure. A foaming composition can be provided comprising about 0.5% to about 5.0% (w/v) levulinic acid and about 1.0 to about 3.0% (w/v) SDS. In one embodiment the foaming composition comprises about 0.5% to about 3.0% (w/v) levulinic acid and about 2.0% (w/v) SDS. Furthermore, a composition comprising 3% levulinic acid plus 1% SDS can come in contact with skin without the irritation caused by other organic acids.

In a further embodiment a method for rapid killing of microbial strains present in liquids or on surfaces contaminated with feces and/or other animal fluids (e.g., urine or saliva) or animal materials (e.g. feathers, hair) is also provided. The method comprises contacting the liquid or surface with a composition comprising an organic acid, selected from the group consisting of lactic acid, acetic acid, and levulinic acid, and SDS, wherein the composition comprises a maximum concentration of 3% by weight levulinic acid and 2% by weight SDS. In one embodiment the composition used comprises levulinic acid and a surfactant.

The reduction of pathogens, including *Salmonella* and *E. coli* O157:H7, resulting from the use of the compositions disclosed herein is a log reduction (>5 log/ml or greater within one minute), not a percent reduction as reported and approved by prior art formulations of organic acids. The bactericidal effects of organic acids have been documented. However these prior art formulations have never been USDA approved for application. The main reasons include doubtable bactericidal results when applied in the product lines, sensory or surface color changes of the treated products, short shelf-life, cost control and difficulty with regards to management or practice. The mere percentage reduction obtained with the prior art formulations, such as for instance, those obtained through the use of citric acid, is simply too little, and thus such compositions fail to provide an efficient or reliable means for safeguarding foods. The present compositions represent the first reliable approach to eliminate *Salmonella* from the poultry products and *E. coli* O157:H7 from the meat and fresh produce.

Methods of reducing resident microbial populations on the surface of a food is provided. In one embodiment the food to be treated is selected form the group consisting of produce, meat, eggs, seafood and fish. The method comprises the step of contacting a food or a food processing surface with a composition comprising levulinic acid and a surfactant, wherein the concentration of each of said levulinic acid and surfactant is at a concentration 0.5×, 0.25×, 0.1×, or less than 0.1× of the concentration required to produce a significant reduction (e.g., greater than one log reduction within 5 minutes) in an *E. coli* O157:H7 microbial population when used separately.

In one embodiment the surface of the food is contacted with the levulinic acid/surfactant containing solution for a predetermined length of time, including lengths of time of 1, 2, 3, 4, 5 or 10 minutes. Applicants have established that such exposure times can be used without negatively impacting the organoleptic properties of the food. Such time interval have been found to be effective in reducing viable cell counts by at least 3 orders of magnitude. More particularly, applicants have demonstrated that compositions comprising levulinic acid, at a concentration of 3% (w/v) or less, in combination with a surfactant (such as SDS) reduces viable microbe cells counts by a factor of 5 to ≥logs within 1 to 5 minutes of contact under conditions otherwise suitable for microbe growth.

In one embodiment the antimicrobial formulations disclosed herein comprise a combination of levulinic acid at a concentration of about 0.5% to about 3% weight/volume plus a surfactant such as a quaternary ammonium cation or SDS at a concentration of about 0.05% to about 2% weight/volume. A foamed antimicrobial formulations can be provided comprising levulinic acid, at a concentration of about 0.5% to about 3% weight/volume plus a pharmaceutically acceptable surfactant at a concentration of about 0.05% to about 3% by weight/volume. Additional combinations of levulinic acid and a surfactant (e.g., SDS) at different concentrations relative to one another will be prepared based on the desired application. For example, three specific combinations will be developed for treatment of different products. Lower concentration (0.5% by weight levulinic acid plus 0.05% by weight SDS) will be selected for treatment of fragile products, such as spinach, lettuce, tomato and sprouts. Middle concentration (2% by weight levulinic acid plus 1% by weight SDS) will be selected for treatment of vegetables and fruits. Relatively higher concentration (3% by weight levulinic acid plus 2 to 3% by weight SDS) will be selected for treatment of meats, food processing surfaces, and environmental samples, such cages, traffic areas, and transportation vehicles. Fish and seafood can be treated with any of the three concentrations of levulinic acid and SDS as mentioned immediately above. In one embodiment the fish or seafood is treated with a middle concentration (2% by weight levulinic acid plus 1% by weight SDS) of the antimicrobial composition. The compositions will also be formulated as different washing solutions, such as washing for all meats, washing for seafood, washing for fish, washing for vegetables, washing for fruits, and washing for environmental samples.

Formulations based on levulinic acid are cheap, easy to produce, do not produce bad odor, release to environment is friendly, plus studies have been performed in human health area (it is widely added in cigarettes for reduction of nicotine). Both levulinic acid and SDS have been approved for use in food by FDA.

The antimicrobial compositions of the present disclosure can be used to remove biofilms from a solid surface, including for example, a food processing surface. The method comprises contacting the biofilm with the antimicrobial composition, optionally in the form of a foamed composition. In one embodiment the biofilm is contacted with an aqueous composition comprising 0.5% to 3% by weight per volume in water of an organic acid and 0.05% to 2% by weight per volume in water of an ionic surfactant. In one embodiment the organic acid is a monoprotic organic acid comprising a carbon backbone of 4 to 10 or 4 to 6 carbons. More particularly, in one embodiment the organic acid has the general structure of:

I

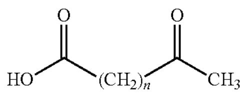

wherein n is an integer selected from 1 to 10. The acid can comprise the structure of formula I wherein n is from 1 to 3. The surfactant can be, but is not limited to, benzalkonium halide, cetylpyridinium chloride, cetylpyridinium bromine, and SDS. An especially useful embodiment of the antimicrobial composition comprises levulinic acid and sodium dodecyl sulfate and/or sodium laureth sulfate. In one embodiment the concentration of the levulinic acid is less than 3%, 2.5%, 2.0%, 1.5%, 1.0%, 0.5% or 0.25% (w/v) of the aqueous composition and the concentration of the sodium dodecyl sulfate and/or sodium laureth sulfate is less than 3.0, 2.0, 1.5, 1.0, 0.5, 0.1 or 0.05% (w/v) of the aqueous composition.

The present antimicrobial compositions can also be used in accordance with one embodiment in a method of treating seeds to remove pathogenic microbes from seeds. The method comprises contacting the seeds with the antimicrobial composition, optionally in the form of a foamed composition. In one embodiment the biofilm is contacted with an aqueous composition comprising 0.5% to 3% by weight per volume in water of an organic acid and 0.05% to 2% by weight per volume in water of an ionic surfactant. In one embodiment the organic acid is a monoprotic organic acid comprising a carbon backbone of 4 to 10 or 4 to 6 carbons. More particularly, in one embodiment the organic acid has the general structure of:

I

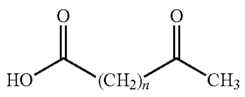

wherein n is an integer selected from 1 to 10. The acid can comprises the structure of formula I wherein n is from 1 to 3. In one embodiment the surfactant is selected from the group consisting of benzalkonium halide, cetylpyridinium chloride, cetylpyridinium bromide, and SDS. In accordance with one embodiment the antimicrobial composition comprises levulinic acid and sodium dodecyl sulfate and/or sodium laureth sulfate.

A method of decontaminating seeds is also provided comprising the steps of contacting the seeds with a composition comprising levulinic acid and a surfactant, wherein the concentration of each of said levulinic acid and surfactant present in said composition is at a concentration 0.5×, 0.25×, 0.1×, or less than 0.1×, of the concentration required to produce a significant reduction (e.g., greater than 50% reduction) in an *E. coli* O157:H7 microbial population when used separatedly. In one embodiment the concentration of the levulinic acid is less than 3%, 2.5%, 2.0%, 1.5%, 1.0%, 0.5% or 0.25% (w/v) of the aqueous composition. In one embodiment the concentration of the levulinic acid is less than 2.5% (w/v) and in a further embodiment the concentration of the levulinic acids is about 0.5% levulinic acid. Furthermore, the concentration of the surfactant is no more than about 0.01% to about 2%, or about 0.01% to about 0.1% and more typically is about 0.05% (w/v). This treatment can be used to eliminate pathogenic organisms such as *E. coli* O157:H7, *Salmonella, Bacillus anthracis, B. cereus* and *Acidovorax avenae* from seeds, and have shown efficacy for killing the spores of such organisms.

In one embodiment of the disclosure, a solution comprising levulinic acid and a surfactants such as SDS, can be added to food items such ground meats, pastes and butters, during the process of manufacturing of said food items, thus providing for an intimate mixture between the food items and the antimicrobial of the disclosure, thus enhancing the safety and shelf-life of those products.

The levulinic compositions have also been added to water used during seed germination and results indicate it does not adversely affect germination. Thus in addition to treating the seeds, the present levulinic acid compositions could be used to eliminate any residual pathogenic organisms (such as *E. coli* O157:H7 and *Salmonella*) that survive an initial treatment of seeds with either 20,000 ppm calcium hypochlorite or the levulinic acid compositions of the present disclosure. This will further safeguard against the possibility of pathogens surviving initial seed treatments and prevent grow of pathogenic organisms in the germination medium. A method of inhibiting the growth of microbes during seed germination is provided wherein the method comprises contacting the seeds prior to, and during the germination of the seeds with a composition comprising levulinic acid and a surfactant. In one embodiment the composition comprises less than 3% levulinic acid and less than 1% of a surfactant.

Aspects of the present disclosure, therefore, encompass embodiments of a method of reducing a microbial population on the surface of a foodstuff, where the method can comprise the step of contacting the foodstuff with an antimicrobial composition, the antimicrobial composition comprising a monoprotic organic acid having a carbon backbone of 4 to 10 carbons, a surfactant, and a solvent, for a time effective in reducing the viability or the cell density of the microbial population on the surface of a foodstuff.

In embodiments of this aspect of the disclosure, the monoprotic organic acid can have the general structure of:

I

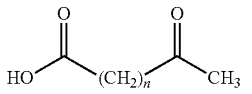

wherein n is an integer from 1 to 6, the total concentration of the monoprotic organic acid can be about 0.1% to about 20% by weight per volume of the antimicrobial composition, and the surfactant can be about 0.1 to 10% by weight per volume of the antimicrobial composition.

In embodiments of this aspect of the disclosure, the monoprotic organic acid can be levulinic acid.

In embodiments of this aspect of the disclosure, the surfactant can be selected from the group consisting of: sodium dodecyl sulfate, sodium laureth sulfate, a quaternary ammonium cation, cetyl pyridinium chloride, and benzalkonium chloride.

In some embodiments of this aspect of the disclosure, the surfactant is sodium dodecyl sulfate.

In some embodiments of this aspect of the disclosure, the monoprotic organic acid can be levulinic acid and the surfactant is sodium dodecyl sulfate.

In embodiments of this aspect of the disclosure, the composition can comprise about 0.3 to about 3% levulinic acid by weight per volume of the antimicrobial composition, and about 0.05% to about 2% sodium dodecyl sulfate by weight per volume of the antimicrobial composition.

In embodiments of this aspect of the disclosure, the antimicrobial composition can be delivered to the foodstuff as a wash, a spray, or a foam.

In embodiments of this aspect of the disclosure, the foodstuff can be a raw foodstuff, a cooked foodstuff, a processed foodstuff, a packaged foodstuff, or any combination thereof.

In embodiments of this aspect of the disclosure, the foodstuff can comprise (i) a plant, a part thereof, a vegetable product, a processed plant product, or any combination thereof, and (ii) a whole animal, an animal carcass, a part thereof, an animal product, milk, an egg, a processed animal product, or any combination thereof.

In embodiments of this aspect of the disclosure, the foodstuff can be a plant, a part thereof, a vegetable product, a processed plant product, or any combination thereof. In these embodiments of this aspect of the disclosure, the foodstuff can be a leaf, a stem, a flower, a seed, a nut, a fruit, a tuber, a root, or any combination thereof.

In embodiments of this aspect of the disclosure, the foodstuff can be a whole animal, an animal carcass, a part thereof, an animal product, milk, an egg, a processed animal product, or any combination thereof.

In embodiments of this aspect of the disclosure, the method can provide a processed foodstuff with antibacterial qualities, said method comprising combining the antimicrobial composition with a raw food material to form a mixture; and processing said mixture to form a processed foodstuff.

In embodiments of this aspect of the disclosure, the raw food material can be an unprocessed meat, and said mixture is then ground.

In embodiments of this aspect of the disclosure, the raw food material can be shelved nuts to form a mixture, and said mixture is then ground for the preparation of a nut butter.

In embodiments of this aspect of the disclosure, the antimicrobial composition can be added to a package with a foodstuff.

The specific examples below are to be construed as merely illustrative, and not limiting of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Bactericidal Efficacy of the Organic Acid/SDS Compositions

Five isolates of *E. coli* O157:H7, including 932 (human isolate), E009 (beef isolate), E0018 (cattle isolate), E0122 (cattle isolate), E0139 (deer jerky isolate); and five isolates of *Salmonella typhimurium* DT104, including three cattle isolates and two meat isolates; and five isolates of *Salmonella enteritidis*, including 564-88 (food isolate), 193-88 (human isolate), E39 (egg isolate), 460-88 (egg isolate) and 457-88 (poultry isolate); and five isolates of *L. monocytogenes*, including LM101 (serotype 4b, salami isolate), LM 112 (serotype 4b, salami isolate), LM113 (serotype 4b, pepperoni isolate), LM9666 (serotype ½ c, human isolate), and LM5779 (serotype ½ c, cheese isolate); and one isolate of *Yersinia pestis* (A1122) were used. Each *Salmonella* and *E. coli* O157:H7 strain was grown in tryptic soy broth (TSB) at 37° C. for 18 h then washed in 0.1 M phosphate buffered saline pH 7.2. Approximately equal cell numbers of each of the five strains were combined and used as a 5-strain mixture with cell numbers being adjusted according to the experimental design. Bacterial cell numbers were confirmed by serial dilutions (1:10) in 0.1% peptone and a volume of 0.1 ml from each dilution tube was plated on tryptic soy agar (TSA), XLD agar, and Sorbitol MacConkey agar (SMA), incubated at 37° C. for 24 h, and colonies were counted.

Acetic acid, caprylic acid, lactic acid, levulinic acid, and sodium dodecyl sulfate (SDS) were tested alone or as a combination at different concentrations and temperatures (8° C. or 21° C.) for their killing effect on *S. enteritidis, S. typhimurium*, and *E. coli* O157:H7 in water or chicken skin contaminated with chicken feces or feathers.

Romaine lettuce, tomato and spinach were purchased from a local retail store. Prior to each study, the produce was tested for *Salmonella*. A volume of 10 ml of sterile water and 10 g lettuce or spinach was added to a Whirl-Pak bag. The sample bag was pummeled in a stomacher blender at 150 rpm for 1 min. The fluid was serially (1:10) diluted in 0.1% peptone and 0.1 ml from each dilution tube was plated in duplicate on XLD plates to determine if these samples were contaminated with *Salmonella*. Only *Salmonella*-negative lettuce, tomato and spinach were used.

Feces from 5 different chickens were used as a mixture. Feathers were obtained from a slaughterhouse. Chicken and poultry wings were purchased from a slaughter plant or local retail store and skin was separated immediately before use. Only *Salmonella*-negative chicken feces, feather, skin, or poultry wing samples were used for the experiments. A volume of 10 ml of deionized water and 1.0 g feces, or feathers, or skin (5×5 $cm^2$) was added to a Whirl-Pak bag. Each bag of feces, feather, or skin sample was pummeled in a stomacher blender at 150 rpm for 1 min. The bag with the poultry wing was massaged by hand for 1 min. The fluid was serially (1:10) diluted in 0.1% peptone and 0.1 ml from each dilution tube was plated in duplicate on XLD plates to determine if these samples were contaminated with salmonellae.

Enumeration of *S. enteritidis, S. typhimurium* DT104 and *E. coli* O157:H7: At each sampling time, 1.0 ml of the treated bacterial suspension was mixed with 9.0 ml of neutralizing buffer or PBS (depending on the pH). The solution was serially (1:10) diluted in 0.1% peptone water and 0.1 ml of each dilution was surface-plated onto TSA and XLD, or TSA and XLD containing ampicillin (32 μg/ml), tetracycline (16 μg/ml) and streptomycin (64 μg/ml) (TSA+, XLD+), or TSA and Sorbitol MacConkey agar plates in duplicate. The plates were incubated at 37° C. for 48 h. Colonies typical of *Salmonella* or *E. coli* O157:H7 were randomly picked from plates with the highest dilution for confirmation of *Salmonella* or *E. coli* by biochemical tests and for confirmation of serotyping by latex agglutination assay. When *Salmonella* or *E. coli* O157:H7 were not detected by direct plating, a selective enrichment in universal pre-enrichment broth (UPB) was performed by incubating 25 ml of treatment suspension in a 500-ml flask containing 225 ml of UPB for 24 h at 37° C. Following pre-enrichment, 1 ml was transferred to 10 ml of selenite cystine broth and incubated for 24 h at 37° C. Following incubation, a 10-μl loopful from the broth tube was plated in duplicate onto XLD plates, and incubated for 24 h at 37° C.

Colonies with typical *Salmonella* spp. morphology were selected and transferred one more time on XLD plates and incubated for 24 h at 37° C. All presumptive *Salmonella* isolates were tested by the *Salmonella* latex agglutination assay. Isolates positive for *Salmonella* by the latex agglutination assay were tested with the API 20E assay for biochemical characteristics for the identification of *Salmonella*. Studies with all chemical treatments were done in duplicate or triplicate, two replicates were plated per sample and results were reported as means.

Example 2

Determination of *Salmonella* and *E. Coli* O157:H7 Inactivation on Lettuce or Spinach Samples of 25 g Romaine lettuce were cut into approximately 5-cm lengths. Whole tomatoes (150 g±10 g) were used. The samples were soaked in *E. coli* O157:H7 or *Salmonella* ($10^8$-$10^9$ CFU/ml) suspension for 60 sec and then air-dried for 20 mins for lettuce and spinach, or 60 mins for tomato, in a laminar hood. The samples were then soaked in a 1000-ml glass beaker containing 500 ml chemical solution or in a 500-ml glass beaker containing 200 ml chemical solution with agitation at 100 rpm by a magnetic bar at 21° C. Following treatment, the sample was placed in a stomacher bag containing 10 ml PBS and pummeled for 1 minute at 150 rpm in a stomacher or in a shaker. The solution was serially (1:10) diluted in 0.1% peptone and a volume of 0.1 ml from each dilution tube was plated on the surface of TSA and XLD for *S. Enteritidis*, TSA and XLD, XLD+ for *S. typhimurium* DT 104 and TSA and SMA for *E. coli* O157:H7 in duplicate for bacterial enumeration.

Determination of *Salmonella* Inactivation in Water Contaminated with Chicken Feathers or Feces:

The protocols used were the same as described previously (Zhao, et al. 2006), with minor modifications. Chicken feathers or feces were weighed and added into a glass beaker containing chemicals to be determined according to different ratios (w/v) in a glass beaker and mixed by a magnetic bar with agitation at 150 rpm. A 5-strain mixture of *S. enteritidis* was added. A volume of 1 ml sample was removed and serially diluted (1:10) in PBS. The aerobic bacterial and *Salmonella* counts were determined according to the procedures we described above.

Determination of *Salmonella* Inactivation on Poultry Wings.

Chicken wings (each approximately 12 cm long, 7 cm wide, and approximately 85 to 90 g) were submerged in a glass beaker containing 500 ml of *S. enteritidis* (about $10^8$ CFU/ml) for 60 sec. Inoculated wings were air dried for 20 min in a laminar flow hood and then individually placed in a Whirl-Pak bag containing 200 ml of chemical solution for 0, 1, 2, 5, 10, 20, 30, and 60 min. The bags were agitated in a vertical shaker at 150 rpm with intermittent hand massage. Following chemical treatment, each chicken wing was placed in a Whirl-Pak bag containing 50 ml of 0.1 M PBS. The bag was agitated in a vertical shaker for 2 min at 150 rpm with intermittent hand massage. The cell suspension (1 ml) was serially (1:10) diluted in 9 ml of 0.1% peptone, and 0.1-ml portions of each dilution was surface plated in duplicate on XLD and TSA plates. The plates were incubated at 37° C. for 24 h or 48 h to enumerate the bacterial number.

Determination of *Salmonella* Inactivation on Chicken Skin.

Chicken skin was separated and cut into a 5×5-$cm^2$ square per sample immediately before the experiment. *S. enteritidis* at $10^7$-$10^8$ CFU with and without feces were inoculated onto the skin and air-dried under a laminar flow hood for 20 minutes. The inoculated skin was placed into a stomacher bag containing the antimicrobial solution (200 ml solution for each skin sample) at 21° C. for a contact time of 0, 1, 3, 5, 10, and 20 minutes with hand massage intermittently (every 30 seconds) or pummeled by a stomacher at 150 rpm. The samples were placed in Whirl-Pak bags, each containing 9 ml PBS then pummeled in a stomacher blender at 150 rpm for 1 min. *Salmonella* were enumerated according to the procedures described above.

Results:

Determination of *Salmonella* inactivation in water with 0.1 to 2.0% by weight levulinic acid revealed about a 1-log CFU/ml reduction. Its killing effect was greater when the levulinic acid concentration was increased to 3.0% by weight, resulting in a 3.4-log *Salmonella*/ml reduction when in contact for 30 minutes, as shown in Table 1. Treatments of 0.5% by weight acetic acid and 0.5% by weight lactic acid for 30 minutes reduced *Salmonella* cell numbers by 0.7- and 2.0-log CFU/ml, respectively. A treatment of 0.05% by weight SDS for 30 minutes did not reduce *Salmonella* cell numbers, as shown in Table 1.

TABLE 1

Reduction of *S. enteritidis* in water treated with organic acids and SDS at 21° C.

| | *S. enteritidis* counts (log CFU/ml) at mins: | | | | | |
|---|---|---|---|---|---|---|
| Chemical Treatment | 0 | 2 | 5 | 10 | 20 | 30 |
| *S. enteritidis* only (pH 6.7) (Control) | 7.2 | 7.0 | 7.1 | 7.2 | 7.0 | 7.2 |
| 0.1% levulinic acid (pH 2.5) | 7.1 | 7.1 | 6.9 | 7.0 | 6.9 | 6.9 |
| 0.5% levulinic acid (pH 2.6) | 7.1 | 6.8 | 6.9 | 6.9 | 6.6 | 6.7 |
| 1.0% levulinic acid (pH 2.9) | 6.9 | 6.7 | 6.8 | 6.9 | 6.9 | 6.7 |
| 1.5% levulinic acid (pH 2.8) | 6.7 | 6.7 | 6.8 | 6.7 | 6.4 | 6.5 |
| 2.0% levulinic acid (pH 2.8) | 6.7 | 6.7 | 6.7 | 6.8 | 6.5 | 6.0 |
| 2.5% levulinic acid (pH 2.6) | 6.9 | 6.8 | 6.9 | 6.4 | 5.8 | 4.8 |
| 3.0% levulinic acid (pH 2.7) | 6.6 | 6.8 | 6.5 | 6.2 | 5.1 | 3.8 |
| 0.5% acetic acid (pH 3.1) | 7.1 | 7.0 | 6.8 | 6.7 | 6.6 | 6.5 |
| 0.5% lactic acid (pH 2.6) | 6.5 | 6.1 | 5.9 | 5.8 | 5.5 | 5.2 |
| 0.05% sodium dodecyl sulfate (pH 4.4) | 7.1 | 7.0 | 7.2 | 7.1 | 7.2 | 7.1 |
| 0.3% levulinic acid + 0.05% SDS (pH 3.1) | –[a] | – | – | – | – | – |
| 0.4% levulinic acid + 0.05% SDS (pH 2.9) | – | – | – | – | – | – |

TABLE 1-continued

Reduction of *S. enteritidis* in water treated with organic acids and SDS at 21° C.

| | *S. enteritidis* counts (log CFU/ml) at mins: | | | | | |
|---|---|---|---|---|---|---|
| Chemical Treatment | 0 | 2 | 5 | 10 | 20 | 30 |
| 0.5% levulinic acid + 0.05% SDS (pH 3.0) | – | – | – | – | – | – |
| 0.5% levulinic acid + 0.03% SDS (pH 3.0) | – | – | – | – | – | – |
| 0.05% caprylic acid + 0.03% SDS (pH 3.4) | – | – | – | – | – | – |
| 0.05% caprylic acid + 0.05% SDS (pH 3.2) | – | – | – | – | – | – |
| 0.5% acetic acid + 0.05% SDS (pH 3.0) | – | – | – | – | – | – |
| 0.5% lactic acid + 0.05% SDS (pH 2.5) | – | – | – | – | – | – |

[a]–, negative by enrichment culture.

All the combinations of organic acids evaluated in combination with 0.03-0.05% by weight SDS were effective, at different degrees, in killing *Salmonella*, with the population of *Salmonella* quickly reduced from $10^7$ CFU/ml to undetectable (enrichment-negative) with a contact time of 5-10 secs.

Neither levulinic acid at 0.5% by weight nor SDS at 0.05% by weight when applied individually provided a significant killing effect on either *E. coli* O157:H7 or *S. typhimurium* DT 104; however, the combination of levulinic acid and SDS at these concentrations reduced *E. coli* O157:H7 and *S. typhimurium* cell numbers by 7 log CFU/ml within 1 min, as shown in Tables 2-4.

TABLE 2

Reduction of *E. coli* O157:H7 in water treated with levulinic acid and SDS at 21° C.

| | *E. coli* O157:H7 counts (log CFU/ml) at min: | | | | | | | |
|---|---|---|---|---|---|---|---|---|
| Chemical Treatment | 0 | 1 | 2 | 5 | 10 | 20 | 30 | 60 |
| *E. coli* O157:H7 only (Control) | 7.1 | 7.2 | 7.0 | 7.2 | 7.1 | 7.1 | 7.2 | 7.2 |
| 0.5% levulinic acid-(pH 3.0) | 7.0 | 6.7 | 6.8 | 6.7 | 6.9 | 6.8 | 6.8 | 6.4 |
| 0.05% SDS-(pH 7.0) | 7.1 | 6.9 | 7.1 | 7.0 | 6.9 | 6.9 | 7.1 | 7.0 |
| 0.5% levulinic acid + 0.05% SDS-(pH 3.0) | –[a] | – | – | – | – | – | – | – |

[a]–, negative by enrichment culture

TABLE 3

Bactericidal effect of different chemical combinations on *E. coli* O157:H7 at 21° C.

| | *E. coli* O157:H7 count (log CFU/ml) at min | | | | | |
|---|---|---|---|---|---|---|
| Chemical combinations | 0 | 1 | 2 | 5 | 10 | 20 |
| $H_2O$ only | ND[a] | ND | ND | ND | ND | 7.3 |
| 0.5% levulinic acid + 0.05% SDS, pH 3.0 | –[b] | – | – | – | – | – |
| 0.5% levulinic acid + 0.05% EDTA, pH 3.1 | 7.1 | 7.1 | 7.1 | 7.1 | 7.1 | 7.1 |

TABLE 3-continued

Bactericidal effect of different chemical combinations on *E. coli* O157:H7 at 21° C.

| Chemical combinations | *E. coli* O157:H7 count (log CFU/ml) at min 0 | 1 | 2 | 5 | 10 | 20 |
|---|---|---|---|---|---|---|
| 0.5% levulinic acid + 0.05% Tween 20, pH 3.0 | 7.1 | 7.1 | 7.1 | 7.1 | 6.9 | 6.8 |
| 0.5% levulinic acid + 0.05% Tween 80, pH 2.9 | 7.4 | 7.4 | 7.4 | 7.4 | 7.2 | 7.2 |

[a]ND, not determined.
[b]*E. coli* O157:H7—negative by enrichment culture assay (<1 CFU/ml). One ml of $10^9$ CFU/ml of *E. coli* O157:H7 was added and mixed for 5-10 sec; it required approximately 12-15 sec to process the reaction mixture of *E. coli* O157 with the treatment solution. Hence, 7.3 to 7.4 log *E. coli* O157:H7/ml was killed by the levulinic acid plus SDS treatment with 15 seconds of exposure.

TABLE 4

Reduction of *S. typhimurium* DT 104 in water treated with levulinic acid + SDS at 21° C.

| Chemical Treatment | *S. typhimurium* DT 104 counts (log CFU/ml) at min: 0[a] | 1 | 2 | 5 | 10 | 20 | 30 | 60 |
|---|---|---|---|---|---|---|---|---|
| *S. typhimurium* only (Control) | 6.9 | 7.0 | 7.0 | 7.0 | 7.0 | 6.9 | 7.0 | 7.0 |
| 0.5% levulinic acid (pH 3.0) | 6.8 | 6.7 | 6.6 | 6.5 | 6.7 | 6.6 | 6.4 | 5.9 |
| 0.05% SDS (pH 7.0) | 7.0 | 7.0 | 6.8 | 6.9 | 6.8 | 6.9 | 6.9 | 6.9 |
| 0.5% levulinic acid + 0.05% SDS (pH 3.0) | +[a] | −[b] | − | − | − | − | − | − |

[a]+, positive by enrichment (minimum detection level is 0.7 log CFU/ml)
[b]−, negative by enrichment culture The antimicrobial activity of levulinic acid and SDS on *Salmonella* on fresh produce and chicken skin was determined. *S. enteritidis* cell numbers on lettuce were reduced by about 4 log CFU/g when treated for 1 min with 0.3% by weight levulinic acid plus 0.05% by weight SDS, and *S. typhimurium* on lettuce or spinach was reduced by about 4 log CFU/g when treated for 1 min with 0.5% by weight levulinic acid and 0.05% by weight SDS, respectively. *E. coli* O157:H7 on lettuce was reduced by 4.5 log CFU/g when treated for 1 min with 0.5% by weight levulinic acid and 0.05% by weight SDS, as shown in Table 5.

TABLE 5

Reduction in *S. enteritidis*, *E. coli* O157:H7 and *S. typhimurium* DT 104 after levulinic acid + SDS treatment on fresh produce or chicken skin at 21° C.

| Treatment | *S. enteritidis* counts (log CFU/ml) at min: 0 | 1 | 2 | 5 | In treatment solution (5 min) |
|---|---|---|---|---|---|
| Romaine Lettuce Treatment | | | | | |
| *S. enteritidis* on lettuce + PBS | 7.7 | 7.3 | 7.4 | 7.3 | 7.4 |
| 0.3% levulinic acid + 0.05% SDS (pH 3.1) | 3.1 | 3.1 | 2.7 | 2.6 | <0.7[a] |
| *S. typhimurium* DT 104 on lettuce + PBS | 7.4 | 7.3 | 7.4 | 7.3 | 7.4 |
| 0.5% levulinic acid + 0.05% SDS (pH 3.1) | 2.8 | 2.9 | 2.9 | 2.7 | <0.7 |
| 3% levulinic acid + 1% SDS (pH 2.7) | <0.7 | <0.7 | <0.7 | <0.7 | <0.7 |
| *E. coli* O157:H7 on lettuce + PBS | 7.4 | 7.5 | 7.2 | 7.2 | 7.4 |
| 0.5% levulinic acid + 0.05% SDS (pH 3.0) | 3.1 | 3.0 | 3.0 | 2.9 | <0.7 |
| 3% levulinic acid + 1% SDS (pH 2.7) | <0.7 | <0.7 | <0.7 | <0.7 | <0.7 |
| Spinach Treatment | | | | | |
| *S. typhimurium* DT 104 on spinach + PBS | 8.0 | 7.9 | 8.1 | 7.9 | 7.9 |
| 0.5% levulinic acid + 0.05% SDS (pH 3.0) | 4.3 | 3.8 | 4.4 | 4.7 | <0.7 |
| Chicken Skin Treatment | | | | | |
| *S. enteritidis* on chicken skin | 7.1 | 7.3 | 7.2 | 7.0 | 6.8 |
| 0.5% levulinic acid + 0.05% SDS (pH 3.0) | 6.7 | 4.4 | 3.5 | 0.7 | <0.7 |

[a]Minimum detection level by direct plating method.

When the concentration of levulinic acid was increased to 3% by weight and SDS to 1% by weight, their antimicrobial activity on lettuce also increased. All inoculated *E. coli* O157:H7 and *S. typhimurium* cells were inactivated to undetectable levels within 1 min with this treatment (Table 5).

Studies with chicken skin revealed *S. enteritidis* was reduced by 6.3 log CFU/g when treated for 5 min with 0.5% by weight levulinic acid and 0.05% by weight SDS (Table 5).

Both *Salmonella* and *E. coli* O157:H7 were undetectable by the direct plating method in the chemical solutions after they were used for treatment of fresh produce or chicken skin (Table 5).

The levulinic acid and SDS treatment to kill *S. enteritidis* was further tested in water containing chicken feathers or feces. Results revealed that feather contamination did not reduce the killing effect of that treatment, whereas the presence of chicken feces did. *S. enteritidis* was reduced from 7.6 log CFU/ml to 1.2 log CFU/ml in chicken feces contaminated water after 2 min exposure, but was not detected (7.6 log CFU/ml reduction) after 5 min ($P<0.05$; Table 6).

TABLE 6

*S. enteritidis* counts for treatment of levulinic acid plus SDS in water containing chicken feathers or feces at 21° C.

| Treatment | *S. enteritidis* counts (log CFU/ml) at min: 0 | 2 | 5 | 10 | 20 | 30 |
|---|---|---|---|---|---|---|
| In water containing chicken feathers (1:100 w/v) | | | | | | |
| *S. enteritidis* (pH 6.7) only | 7.5 | 7.7 | 7.4 | 7.5 | 7.6 | 7.6 |
| 1.0% levulinic acid + 0.1% SDS (pH 3.2) | <0.7 | <0.7 | <0.7 | <0.7 | <0.7 | <0.7 |
| In water containing chicken feces (1:100 w/v) | | | | | | |
| *S. enteritidis* only (pH 6.8) | 7.6 | 7.5 | 7.5 | 7.6 | 7.5 | 7.6 |
| 1.0% levulinic acid + 0.1% SDS (pH 4.0) | 4.9 | 1.2 | <0.7 | <0.7 | <0.7 | <0.7 |
| In water containing chicken feces (1:20 w/v) | | | | | | |
| *S. enteritidis* only (pH 6.7) | 7.7 | 7.8 | 7.7 | 7.7 | 7.7 | 7.6 |
| 3.0% levulinic acid + 2.0% SDS (pH 4.0) | <0.7 | <0.7 | <0.7 | <0.7 | <0.7 | <0.7 |

<0.7: Minimum detection level by direct plating method

Greater concentrations of levulinic acid and SDS were more effective in killing *Salmonella*, even in water heavily contaminated with chicken feces (1 part feces: 20 parts water; wt/v) (Table 6).

Aerobic bacteria counts in water contaminated with chicken feces at a ratio of 1:100 (w/v) were reduced by greater than 4.0 log CFU/ml after treatment with 1% by weight levulinic acid and 0.1% by weight SDS for 2 min. The antimicrobial effect was increased to about 5.5 log CFU/ml reduction in water contaminated with chicken feces at a ratio of 1:20 (w/v) when the chemical concentrations were increased to 3% by weight levulinic acid plus 2.0% by weight SDS for 2 min, as shown in Table 7.

TABLE 7

Aerobic bacteria counts after levulinic acid + SDS in water containing chicken feces at 21° C.

| | Bacteria counts (log CFU/ml) at min: | | | | | |
|---|---|---|---|---|---|---|
| Treatment | 0 | 2 | 5 | 10 | 20 | 30 |
| In water containing chicken feces (1:100, w/v) | | | | | | |
| Aerobic bacteria only | 7.4 | ND[a] | ND | 7.4 | 7.4 | 7.4 |
| 1.0% levulinic acid + 0.1% SDS (pH 4.0) | 5.0 | 3.0 | 2.9 | 2.9 | 2.0 | 2.0 |
| In water containing chicken feces (1:20, w/v) | | | | | | |
| Aerobic bacteria only | 10.4 | 10.4 | 10.3 | 10.4 | 10.4 | 10.4 |
| 3.0% levulinic acid + 2.0% SDS (pH 4.0) | 4.5 | 4.9 | 5.1 | 4.9 | 5.1 | 5.1 |

[a]ND, Not determined.

Example 3

TABLE 8

*Salmonella* and aerobic bacteria after levulinic acid + SDS on poultry wings at 8° C.

| Treatment | *S. enteritidis* counts (log CFU/ml) at min: | | | | |
|---|---|---|---|---|---|
| | 0 | 1 | 2 | 5 | In treatment solution (5 min) |
| PBS (7.2) | 6.5 | ND[a] | ND | 6.5 | 7.6 |
| 3% levulinic acid + 2% SDS (pH 2.7) | 6.1 | <0.7[b] | <0.7 | <0.7 | <0.7 |

TABLE 8-continued

*Salmonella* and aerobic bacteria after levulinic acid + SDS on poultry wings at 8° C.

| Treatment | Aerobic bacteria counts (log CFU/ml) at min: | | | | |
|---|---|---|---|---|---|
| | 0 | 1 | 2 | 5 | In treatment solution (5 min) |
| PBS (pH 7.2) | 7.9 | N/A | N/A | 8.5 | 9.8 |
| 3% levulinic acid + 2% SDS (pH 2.7) | 7.8 | <0.7 | <0.7 | <0.7 | <0.7 |

[a]ND, not determined

[b]Minimum detection level by direct plating method

TABLE 9

Counts of *S. enteritidis* on chicken wings treated with levulinic acid + SDS at 8° C.

| | Means (±SD) bacterial counts (log CFU/cm2) at minute: | | | |
|---|---|---|---|---|
| Treatment | 0 | 1 | 5 | In treatment solution (5 min) |
| *S. enteritidis* only | 7.8 ± 0.0 | 7.0 ± 0.2 | 6.8 ± 0.1 | 7.3 ± 0.1 |
| 2.0% levulinic acid + 1.0% SDS | 7.3 ± 0.2 | 4.4 ± 0.1 | 3.2 ± 0.2 | + |
| *S. enteritidis* only | 7.4 ± 0.1 | 6.7 ± 0.4 | 7.0 ± 0.2 | 6.9 ± 0.1 |
| 3.0% levulinic acid + 1.0% SDS | 7.4 ± 0.2 | 2.7 ± 0.1 | 2.2 ± 0.2 | – |
| *S. enteritidis* only | 6.5 ± 0.5 | 6.7 ± 0.4 | 6.5 ± 0.3 | 7.6 ± 0.0 |
| 3.0% levulinic acid + 2% SDS | 6.1 ± 0.2 | + | – | – |

+, positive by enrichment culture but not by direct plating (minimum detection level is 1.7 log CFU/ml)

–, negative by direct plating and enrichment culture

Example 4

The antimicrobial activity of 0.5% levulinic acid plus 0.05% SDS against a variety of different bacteria in pure culture was determined and results revealed it had broad spectrum antimicrobial activity against all of the bacteria evaluated, as shown in Table 10. Included were *Staphylococcus aureus, Shigella sonnei, Campylobacter jejuni*, and STEC O26:H11 and O111:NM, with greater than 6-log reductions within 1 min at 21° C.

TABLE 10

Effect of 0.5% levulinic acid + 0.05% SDS, pH 3.1 at 21° C. on bacterial species

| | Bacterial counts (log CFU/ml) at min: | | | | | | | |
|---|---|---|---|---|---|---|---|---|
| Bacterial Name | 0[a] | 1 | 2 | 5 | 10 | 20 | 30 | 60 |
| *Klebsiella pneumonia* in 0.1M PBS (Control) | ND[b] | ND | ND | 6.5 | ND | ND | ND | 6.6 |
| *K. pneumonia* in 0.5% levulinic acid + 0.05% SDS (pH 3.1) | —[c] | — | — | — | — | — | — | — |
| *Hafinia alvei* in 0.1M PBS (control) | ND | ND | ND | 6.9 | ND | ND | ND | 6.9 |
| *H. alvei* in 0.5% levulinic acid + 0.05% SDS (pH 3.1) | — | — | — | — | — | — | — | — |
| *Klebsiella oxytoca* in 0.1M PBS (Control) | ND | ND | ND | 7.2 | ND | ND | ND | 7.1 |
| *K. oxytoca* in 0.5% levulinic acids + 0.05% SDS (pH 3.1) | — | — | — | — | — | — | — | — |
| *Proteus hauseri* in 0.1M PBS (Control) | ND | ND | ND | 7.3 | ND | ND | ND | 7.4 |
| *Pr. hauseri* in 0.5% levulinic acid + 0.05% SDS (pH 3.1) | — | — | — | — | — | — | — | — |

TABLE 10-continued

Effect of 0.5% levulinic acid + 0.05% SDS, pH 3.1 at 21° C. on bacterial species

| Bacterial Name | Bacterial counts (log CFU/ml) at min: 0[a] | 1 | 2 | 5 | 10 | 20 | 30 | 60 |
|---|---|---|---|---|---|---|---|---|
| *Serratia marcesens* in 0.1M PBS (Control) | ND | ND | ND | 7.3 | ND | ND | ND | 7.3 |
| *Ser. marcesens* in 0.5% levulinic acids + 0.05% SDS (pH 3.1) | — | — | — | — | — | — | — | — |
| *Shigella flexneri* in 0.1M PBS (Control) | ND | ND | ND | 7.1 | ND | ND | ND | 7.1 |
| *Shi. flexneri* in 0.5% levulinic acid + 0.05% SDS (pH 3.1) | — | — | — | — | — | — | — | — |
| *Shi. sonnei* in 0.1M PBS (Control) | ND | ND | ND | 7.3 | ND | ND | ND | 7.3 |
| *Shi. sonnei* in 0.5% levulinic acid + 0.05% SDS (pH 3.1) | — | — | — | — | — | — | — | — |
| *Staphylococcus aureus* in 0.1M PBS (Control) | ND | ND | ND | 6.9 | ND | ND | ND | 6.9 |
| *Staph. aureus* in 0.5% levulinic acid + 0.05% SDS (pH 3.1) | — | — | — | — | — | — | — | — |
| *Aerococcus viridans* in 0.1M PBS (control) | ND | ND | ND | 6.0 | ND | ND | ND | 6.0 |
| *Aero. viridans* in 0.5% levulinic acid + 0.05% SDS (pH 3.1) | — | — | — | — | — | — | — | — |
| *Yersinia pseudotubersulosis* in 0.1M PBS (control) | ND | ND | ND | 7.0 | ND | ND | ND | 7.0 |
| *Y. pseudotubersulosis* in 0.5% levulinic acids + 0.05% SDS (pH 3.1) | — | — | — | — | — | — | — | — |
| *E. coli* O26:H11 in 0.1M PBS (Control) | ND | ND | ND | 7.2 | ND | ND | ND | 7.2 |
| *E. coli* O26:H11 in 0.5% levulinic acid + 0.05% SDS (pH 3.1) | — | — | — | — | — | — | — | — |
| *E. coli* O111:NM in 0.1M PBS (Control) | ND | ND | ND | 7.1 | ND | ND | ND | 7.1 |
| *E. coli* O111:NM in 0.5% levulinic acid + 0.05% SDS (pH 3.1) | — | — | — | — | — | — | — | — |
| *Vibrio chloerae* in 0.1M PBS (control) | ND | 5.1 | 5.0 | ND | ND | ND | 4.2 | ND |
| *V. chloerae* in 0.5% levulinic acid + 0.05% SDS (pH 3.1) | — | — | — | — | — | — | — | — |
| *Campylobacter jejuni* in 0.1M PBS (control) | 8.2 | 8.3 | 8.1 | 8.0 | 8.4 | 8.1 | 8.2 | 8.4 |
| *Camp. jejuni* in 0.5% levulinic acid + 0.05% SDS (pH 3.1) | <0.7 | <0.7 | <0.7 | <0.7 | <0.7 | <0.7 | <0.7 | <0.7 |

ND = Not Determined; a dash "—" indicates "not detected"

[a]Initial inoculation level: *Hafinia alvei*: $1.9 \times 10^8$ CFU/ml; *K. oxytoca*: $2.1 \times 10^9$ CFU/ml; *Pr. hauseri*: $1.3 \times 10^9$ CFU/ml; *Serr. marcesens*: $1.2 \times 10^9$ CFU/ml; *Shi. flexneri*: $1.1 \times 10^9$ CFU/ml; *Shi. sonnei*: $1.3 \times 10^9$ CFU/ml; *Staph. aureus*: $1.9 \times 10^8$ CFU/ml; *Aero. virians*: $1.0 \times 10^8$ CFU/ml; *Y. pseudotuberculosis*: $1.0 \times 10^9$ CFU/ml; *E. coli* O26:H11: $1.2 \times 10^9$ CFU/ml; *E. coli* O111:NM: $1.1 \times 10^9$; *V. cholerae*: $1.2 \times 10^6$ CFU/ml; *Camp. jejuni*: $1.2 \times 10^{10}$ CFU/ml.

[b]The actual time 0 was delayed by 5 to 10 seconds due to time for sample processing.

[c]ND, not determined.

[d]Negative by direct plating and enrichment culture.

Different combinations of pharmaceutically acceptable acids in combination with various pharmaceutically acceptable surfactants were tested for their antibacterial properties, as indicated in Tables 10 and 11. As indicated by the following data, particularly Table 10, not all organic acids/surfactant combinations perform equivalently with regards to their efficacy as antimicrobial agents.

TABLE 11

Reduction of microorganisms by different chemical combination at 21° C.

| Chemical treatment | 0[a] | 1 | 2 | 5 | 10 | 20 | 30 | 60 |
|---|---|---|---|---|---|---|---|---|
| | *E. coli* O157:H7 counts (log CFU/ml) at min: | | | | | | | |
| *E. coli* O157:H7 only (Control) | 7.2 | 7.4 | ND[b] | 7.3 | ND | ND | 7.3 | 7.4 |
| 0.05% SDS (pH 3.0) | <0.7 | <0.7 | <0.7 | <0.7 | <0.7 | <0.7 | <0.7 | <0.7 |
| | *S. enteritidis* counts (log CFU/ml) at min: | | | | | | | |
| *S. enteritidis* only (Control) | 7.2 | 7.1 | ND | 7.2 | ND | ND | 7.4 | 7.3 |
| 0.05% SDS (pH 3.0) | <0.7 | <0.7 | <0.7 | <0.7 | <0.7 | <0.7 | <0.7 | <0.7 |

TABLE 11-continued

| Reduction of microorganisms by different chemical combination at 21° C. | | | | | | | | |
|---|---|---|---|---|---|---|---|---|
| Chemical treatment | 0[a] | 1 | 2 | 5 | 10 | 20 | 30 | 60 |
| | *Y. pestis* counts (log CFU/ml) at min: | | | | | | | |
| *Y. pestis* only (Control) | 6.3 | 6.1 | 6.4 | 6.7 | 6.6 | 6.5 | 6.7 | 6.7 |
| 0.5% Levulinic acid + 0.05% SDS (pH 3.0) | <0.7 | <0.7 | <0.7 | <0.7 | <0.7 | <0.7 | <0.7 | <0.7 |

[a]The actual time 0 was delayed by 5 to 10 seconds due to time for sample processing.
[b]ND, not determined.
[a]The actual time 0 may was delayed by 10 to 20 seconds due to time for sample processing.
[b]+, Below the minimum detection level by direct plating (<0.7 log CFU/ml), but positive by enrichment culture.

Example 5

Efficacy of the Organic Acid/SDS Compositions Against *L. Monocytogenes*

The efficacy of the antibacterial compositions disclosed herein was tested against *Listeria monocytogenes* using the same assay and procedures disclosed in Example 1. The results are indicated in Table 12.

TABLE 12

| Reduction of *L. monocytogenes* by levulinic acid and SDS individually, and in combination at 21° C. | | | | | | |
|---|---|---|---|---|---|---|
| | *L. monocytogenes* counts (log CFU/ml) at min: | | | | | |
| Chemical Treatment | 0[a] | 2 | 5 | 10 | 20 | 30 |
| 0.5% levulinic acid (pH 3.1) | 6.7 ± 0.2 | 6.7 ± 0.1 | 6.8 ± 0.3 | 6.9 ± 0.2 | 6.7 ± 0.2 | 6.8 ± 0.2 |
| 1.0% levulinic acid (pH 3.0) | 6.8 ± 0.3 | 6.7 ± 0.2 | 6.6 ± 0.3 | 6.6 ± 0.3 | 6.6 ± 0.0 | 6.6 ± 0.3 |
| 1.5% levulinic acid (pH 2.9) | 6.9 ± 0.1 | 6.9 ± 0.2 | 6.9 ± 0.3 | 6.9 ± 0.1 | 6.9 ± 0.3 | 6.8 ± 0.3 |
| 2.0% levulinic acid (pH 2.9) | 6.8 ± 0.3 | 6.8 ± 0.2 | 6.9 ± 0.2 | 6.7 ± 0.2 | 6.9 ± 0.2 | 6.8 ± 0.2 |
| 0.05% sodium dodecyl sulfate (pH 4.8) | 6.6 ± 0.3 | 6.4 ± 0.1 | 6.0 ± 0.1 | 5.0 ± 0.3 | 3.8 ± 0.2 | 3.3 ± 0.1 |
| 0.5% levulinic acid + 0.05% SDS (pH 3.0) | –[c] | – | – | – | – | – |

[a]The actual time 0 was delayed by 5 to 10 seconds due to time for sample processing.
[b]+, Positive by enrichment culture but not by direct plating (minimum detection level is 0.7 log CFU/ml).
[c]–, Negative by direct plating and enrichment culture.

Example 6

The results shown in Tables 13-15 are of special relevance as they indicate the superiority of certain acid/surfactant combinations over others. More particularly, Tables 11-13 indicate that the choice of acid leads to different antimicrobial activity even when different acids are used in the same concentrations. These tables also indicate that the number of protic hydrogen atoms in a given acid is not relevant to the bactericidal activity of the solutions, as illustrated by the different activities observed when $H_4EDTA$ (a tetraprotic acid), citric acid (a triprotic) or fumaric acid (a diprotic acid) are used instead linear-chain mono-acids. This may be due to the smaller acidity of small, multiprotic acids vis-à-vis monoprotic ones, due to inter- and intra-molecular hydrogen bonding and also, in the case of $H_4EDTA$, of intramolecular transfer to two $H^+$ moieties from the carboxyl group to the amine nitrogen.

Taken together, the results described in Tables 13-15 clearly indicate that not all acid/surfactant combinations display optimal antibacterial activity, when both activity time and intensity of the microbicide effect are considered. Those tables suggest that linear, long (>4 carbon atoms) chain, monoprotic acids are preferred over others and ionic, long-chain surfactants (SDS, benzalkonium chloride, and cetylpyridinium chloride) are preferred over non-ionic surfactants (e.g., cocamide MEA).

Chain length may also be relevant as free-standing long-chains are more likely to disrupt cell walls. In the case of multiprotic acids, intramolecular hydrogen bonding may, at least in part, restrain these chains into a locked configuration, less likely to be disruptive of the lipid layer in cell walls. This is in part supported by the greater length of time needed for multiprotic acids to exhibit a measurable effect when compared with linear monoprotic acids.

TABLE 13

| Reduction of *S. enteritidis* and aerobic plate counts on ripen tomato by levulinic acid + SDS treatment at 21° C. | | | | | |
|---|---|---|---|---|---|
| Treatment | | | | | |
| | *S. enteritidis* counts (log CFU/g) at min: | | | | |
| | 0[a] | 1 | 2 | 5 | In treatment solution (5 min) |
| PBS (7.2) (Control) | 5.0 | 4.7 | 4.7 | 4.9 | 5.6 |
| 0.5% levulinic acid + 0.05% SDS (pH 3.1) | 4.0 | 2.4 | 2.4 | 2.6 | +[b] |
| | *S. enteritidis* counts (log CFU/g) at min: | | | | |
| | 0 | 1 | 2 | 5 | In treatment solution (5 min) |

TABLE 13-continued

Reduction of *S. enteritidis* and aerobic plate counts on ripen tomato by levulinic acid + SDS treatment at 21° C.

| Treatment | | | | | |
|---|---|---|---|---|---|
| PBS (pH 7.2) (Control) | 5.2 | 5.0 | 4.7 | 5.0 | 5.8 |
| 0.5% levulinic acid + 0.05% SDS (pH 3.1) | 4.7 | 3.1 | 3.1 | 3.0 | 1.0 |
| | Aerobic plate counts (log CFU/g) at min: | | | | |
| | 0 | 1 | 2 | 5 | In treatment solution (5 min) |
| PBS (7.2) (Control) | 5.8 | 5.5 | 5.2 | 5.1 | 5.9 |
| 1.0% levulinic acid + 0.1% SDS (pH 2.8) | 5.3 | 2.9 | 2.9 | 1.8 | + |
| | *S. enteritidis* counts (log CFU/g) at min: | | | | |
| | 0 | 1 | 2 | 5 | In treatment solution (5 min) |
| PBS (pH 7.2) (Control) | 5.9 | 5.6 | 5.4 | 5.1 | 6.0 |
| 1.0% levulinic acid + 0.1% SDS (pH 2.8) | 5.5 | 3.1 | 3.1 | 2.1 | 3.1 |

TABLE 13-continued

Reduction of *S. enteritidis* and aerobic plate counts on ripen tomato by levulinic acid + SDS treatment at 21° C.

| Treatment | | | | | |
|---|---|---|---|---|---|
| | Aerobic plate counts (log CFU/g) at min: | | | | |
| | 0 | 1 | 2 | 5 | In treatment solution (5 min) |
| PBS (7.2) (Control) | 5.8 | 5.5 | 5.2 | 5.1 | 5.9 |
| 2.0% levulinic acid + 1.0% SDS (pH 2.7) | 4.4 | 1.9 | + | + | + |
| | *S. enteritidis* counts (log CFU/g) at min: | | | | |
| | 0 | 1 | 2 | 5 | In treatment solution (5 min) |
| PBS (pH 7.2) (Control) | 5.9 | 5.6 | 5.4 | 5.1 | 6.0 |
| 2.0% levulinic acid + 1.0% SDS (pH 2.7) | 4.7 | 2.3 | 1.0 | 1.1 | 1.8 |

[a]The actual time 0 may was delayed by 10 to 20 seconds due to time for sample processing.
[b]+, Below the minimum detection level by direct plating ( <0.7 log CFU/ml), but positive by enrichment culture.

TABLE 14

Reduction of *E. coli* O157:H7 by combination of different acids and SDS at 21° C.

| Chemical treatment | Bacterial counts (log CFU/ml) at min: 0[a] | 1 | 2 | 5 | 10 | 20 | 30 | 60 |
|---|---|---|---|---|---|---|---|---|
| *E. coli* O157:H7 only (Control) | 7.7 | 7.6 | 7.7 | 7.7 | 7.8 | 7.7 | 7.8 | 7.7 |
| 0.5% adipic acid + 0.05% benzalkonium chloride (pH 3.1) | 2.7 | 1.7 | +[b] | –[c] | – | – | – | – |
| 0.5% cetylpyidinum chloride + 0.05% SDS (pH 5.8) | + | + | + | + | + | + | + | + |
| 0.5% citric acid + 0.05% SDS (pH 2.5) | + | + | – | – | – | – | – | – |
| 0.5% EDTA + 0.05% SDS (pH 3.0) | – | – | – | – | – | – | – | – |
| 0.5% eugenol + 0.05% SDS (pH 2.6) | – | – | – | – | – | – | – | – |
| 0.5% Fumaric acid + 0.05% SDS (pH 2.4) | + | – | – | – | – | – | – | – |
| 0.5% hexanoic acid + 0.05% SDS (pH 3.2) | 2.7 | 1.7 | – | – | – | – | – | – |
| 0.5% levulinic acid + 0.05% benzalkonium chloride (pH 3.1) | – | – | – | – | – | – | – | – |
| 0.5% levulinic acid + 0.05% cetypridinium chloride (pH 3.1) | – | – | – | – | – | – | – | – |
| 0.5% levulinic acid + 0.05% cocamide MEA (pH 3.1) | >5.3 | >5.3 | >5.3 | >5.3 | >5.3 | >5.3 | >5.3 | >5.3 |
| 0.5% malic acid + 0.05% SDS (pH 2.6) | + | + | – | – | – | – | – | – |
| 0.5% phosphoric acid + 0.05% SDS (pH 1.7) | – | – | – | – | – | – | – | – |
| 0.5% succinic acid + 0.05% SDS (pH 2.9) | – | – | – | – | – | – | – | – |
| 0.5% tartaric acid + 0.05% SDS (pH 2.5) | + | + | + | – | – | – | – | – |

[a]The actual time 0 was delayed by 5 to 10 seconds due to time for sample processing.

[b]+, Positive by enrichment culture but not by direct plating (minimum detection level is 0.7 log CFU/ml).

[c]–, Negative by both direct plating and enrichment culture.

TABLE 15

Reduction of *S. enteritidis* by combination of acids and SDS at 21° C.

| Chemical treatment | Bacterial counts (log CFU/ml) at min: 0[a] | 1 | 2 | 5 | 10 | 20 | 30 | 60 |
|---|---|---|---|---|---|---|---|---|
| *S. enteritidis* only (Control) | 7.5 | 7.6 | 7.4 | 7.6 | 7.5 | 7.4 | 7.6 | 7.5 |
| 0.5% adipic acid + 0.05% benzalkonium chloride (pH 3.1) | +[b] | −[c] | − | − | − | − | − | − |
| 0.5% cetylpyidinum chloride + 0.05% SDS (pH 5.8) | + | + | + | + | + | + | + | + |
| 0.5% citric acid + 0.05% SDS (pH 2.5) | + | + | − | − | − | − | − | − |
| 0.5% EDTA + 0.05% SDS (pH 3.0) | + | + | + | − | − | − | − | − |
| 0.5% eugenol + 0.05% SDS (pH 2.6) | − | − | − | − | − | − | − | − |
| 0.5% Fumaric acid + 0.05% SDS (pH 2.4) | + | + | + | − | − | − | − | − |
| 0.5% hexanoic acid + 0.05% SDS (pH 3.2) | − | − | − | − | − | − | − | − |
| 0.5% levulinic acid + 0.05% benzalkonium chloride (pH 3.1) | − | − | − | − | − | − | − | − |
| 0.5% levulinic acid + 0.05% cetypridinium chloride (pH 3.1) | − | − | − | − | − | − | − | − |
| 0.5% levulinic acid + 0.05% cocamide MEA (pH 3.1) | >5.8 | >5.8 | >5.8 | >5.8 | >5.8 | 5.3 | 4.8 | 4.1 |
| 0.5% malic acid + 0.05% SDS (pH 2.6) | + | + | − | − | − | − | − | − |
| 0.5% phosphoric acid + 0.05% SDS (pH 1.7) | + | − | − | − | − | − | − | − |
| 0.5% succinic acid + 0.05% SDS (pH 2.9) | + | − | − | − | − | − | − | − |
| 0.5% tartaric acid + 0.05% SDS (pH 2.5) | + | + | + | − | − | − | − | − |

[a]The actual time 0 was delayed by 5 to 10 seconds due to time for sample processing.

[b]+, Positive by enrichment culture but not by direct plating (minimum detection level is 0.7 log CFU/ml).

[c]−, Negative by both direct plating and enrichment culture.

Example 7

Efficacy of Compositions to Kill Spores of *Bacillus anthracis* Sterne

For all experiments an equal volume of spore suspension of *B. anthracis* Sterne ($34F_2$) was added to 25 ml of reagents A, B, C, D, E, and F in 250-ml flasks. The compositions of reagents are A: 3% levulinic acid plus 2% SDS; B: 2% levulinic acid plus 1% SDS; C: 0.5% levulinic acid plus 0.05% SDS; D: 3% levulinic acid; E: 2% SDS; F: water (control).

Flasks were incubated at 37° C. in a shaker (200 rpm). At each time point 100 μl of sample was transferred into 900 μl water, vortexed, and 100 μl of the dilution spread on Brain Heart Infusion agar plates. Plates were incubated at 37° C. overnight and colonies counted the next morning (approximately 16 hours later).

Figure 1B:
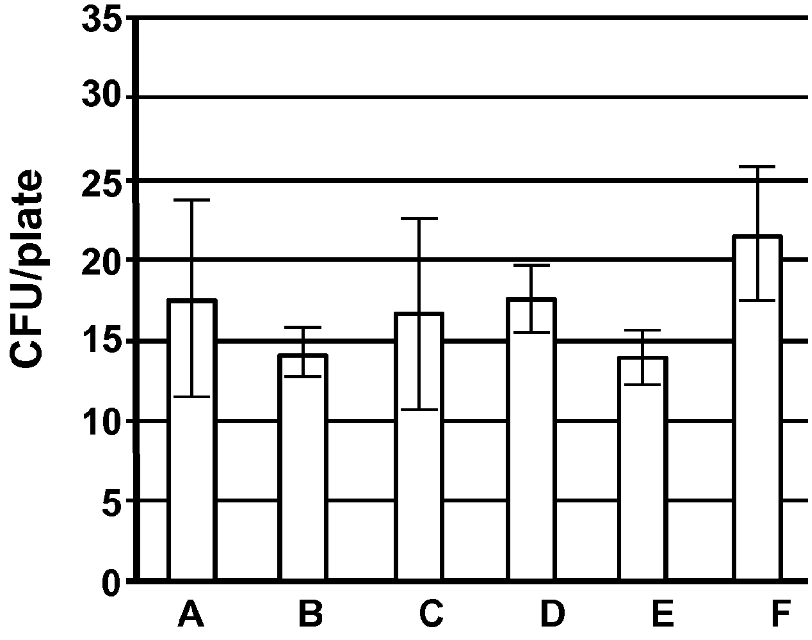
Figure 1C:
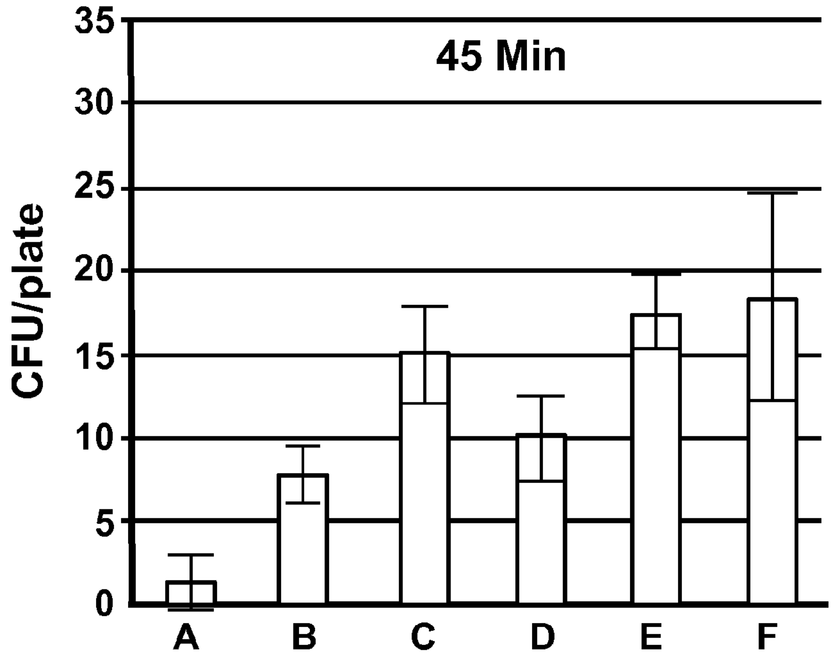
Figure 1D:
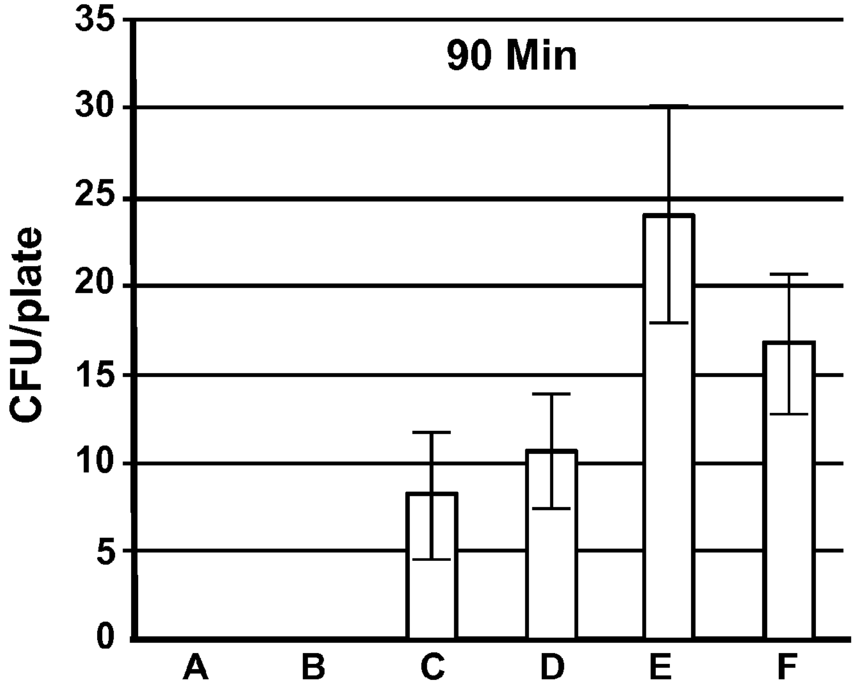
Figure 1E:
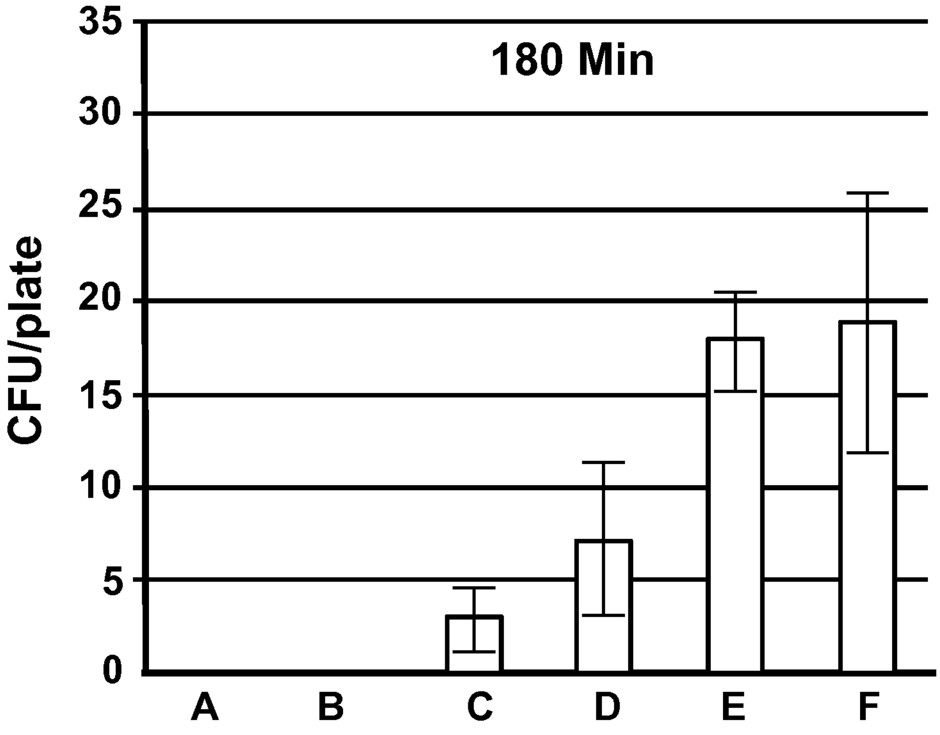
Figure 2A:
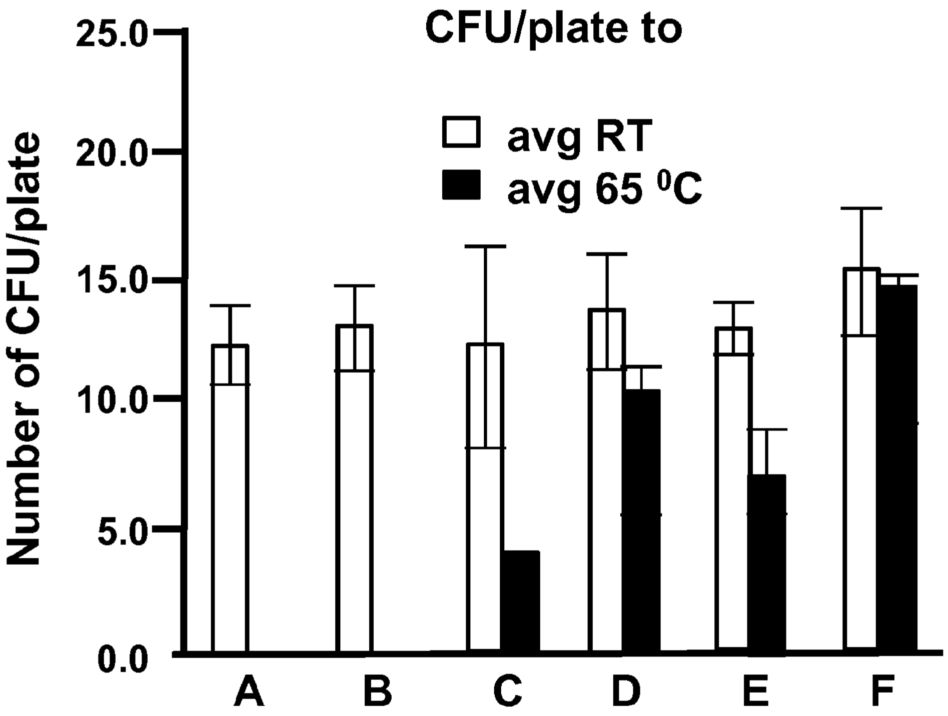
FIGS. 2A-2E illustrate bar graphs demonstrating the efficacy of levulinic acid and SDS, alone or in combination, to kill spores of *Bacillus anthracis* Sterne. Spores were exposed to one of six different solutions: A: 3% levulinic acid plus 2% SDS; B: 2% levulinic acid plus 1% SDS; C: 0.5% levulinic acid plus 0.05% SDS; D: 3% levulinic acid; E: 2% SDS; and F: water (serving as the control) for time intervals before testing the spores for viability relative to the control sample. In order to differentiate whether CFU originated from vegetative cells or from spores, at each time point samples were split in two equivalent aliquots. One aliquot was subjected to heat treatment (65° C., 30 min) to kill vegetative cells before enumeration of residual heat-resistant spores. The other aliquot was plated at room temperature (RT). Average plate counts are based on counting three plates; error bars indicate+/−one standard deviation.
Figure 2B:
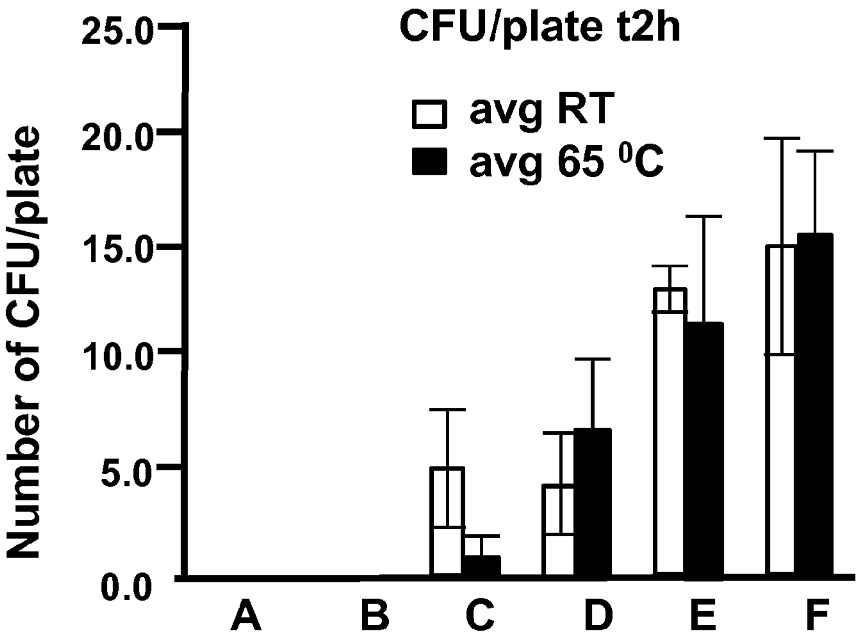
Figure 2C:
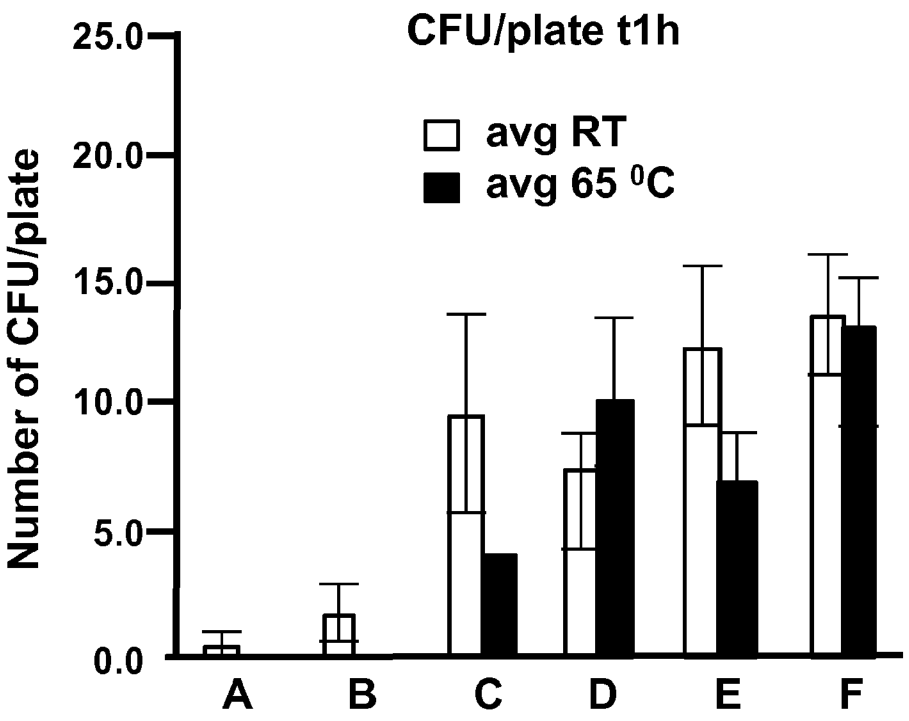
Figure 2D:
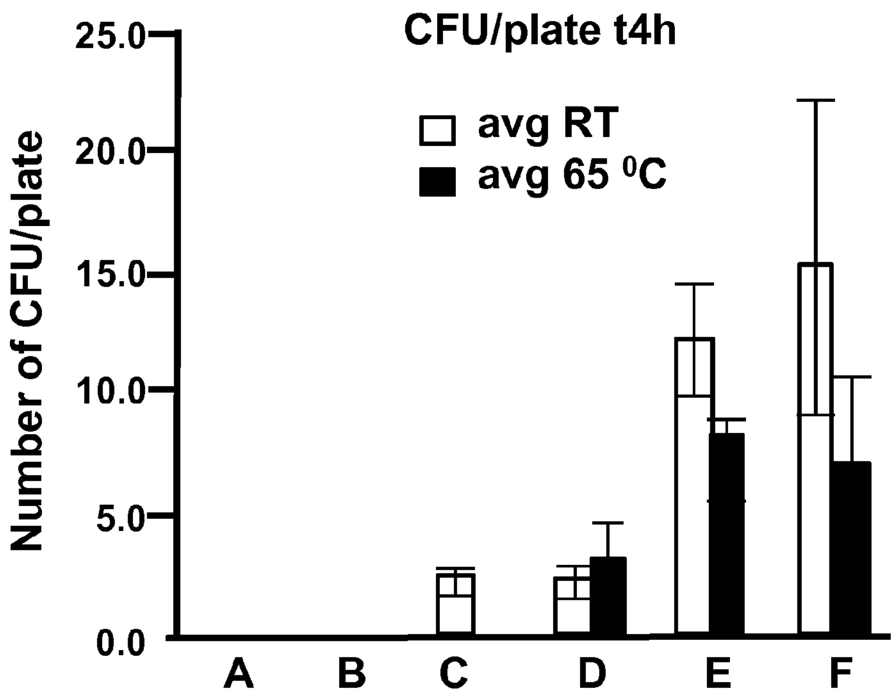
Figure 2E:
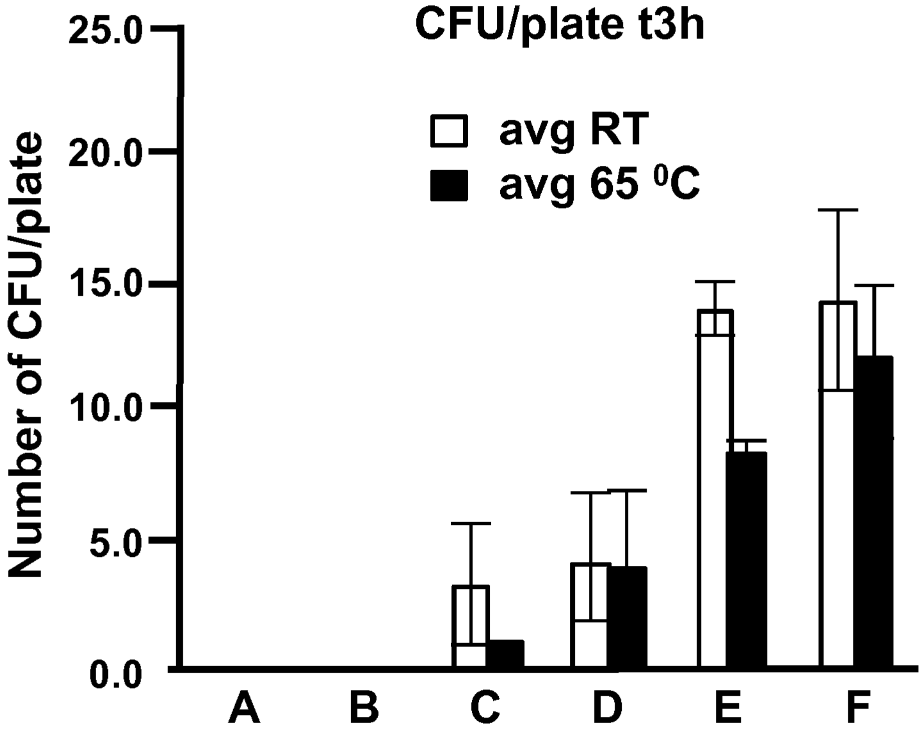
Figure 3A:
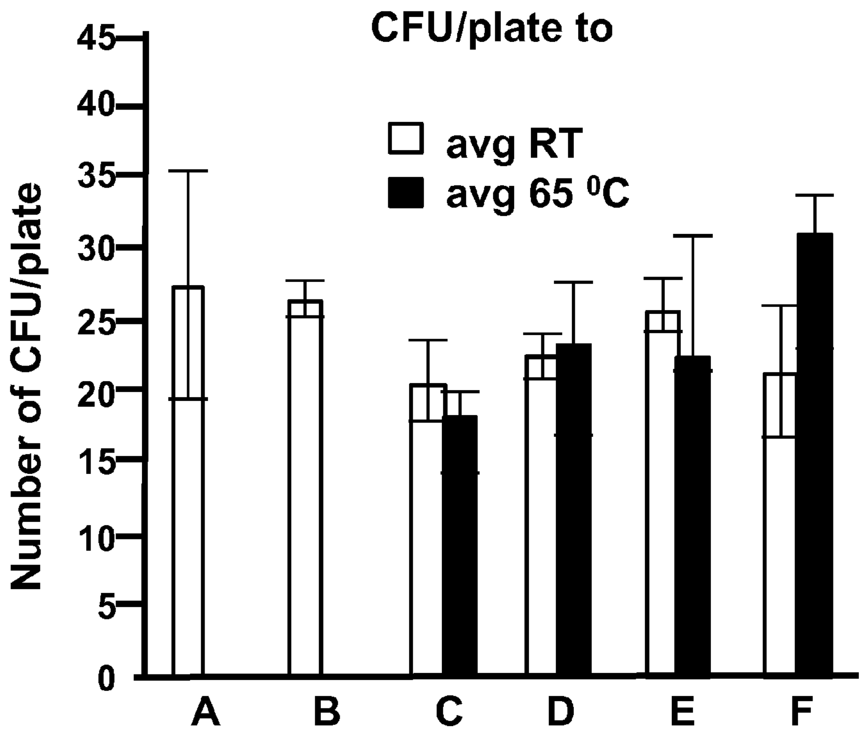
FIGS. 3A-3E represent bar graphs demonstrating the efficacy of levulinic acid and SDS, alone or in combination, to kill spores of *Bacillus anthracis* Sterne. Spores were exposed to one of six different solutions: A: 3% levulinic acid plus 2% SDS; B: 2% levulinic acid plus 1% SDS; C: 0.5% levulinic acid plus 0.05% SDS; D: 3% levulinic acid; E: 2% SDS; and F: water (serving as the control) for time intervals before testing the spores for viability relative to the control sample. In order to differentiate whether CFU originated from vegetative cells or from spores, at each time point samples were split in two equivalent aliquots. One aliquot was subjected to heat treatment (65° C., 30 min) to kill vegetative cells before enumeration of residual heat-resistant spores. The other aliquot was plated at room temperature (RT). Average plate counts are based on counting three plates; error bars indicate+/−one standard deviation.
Figure 3B:
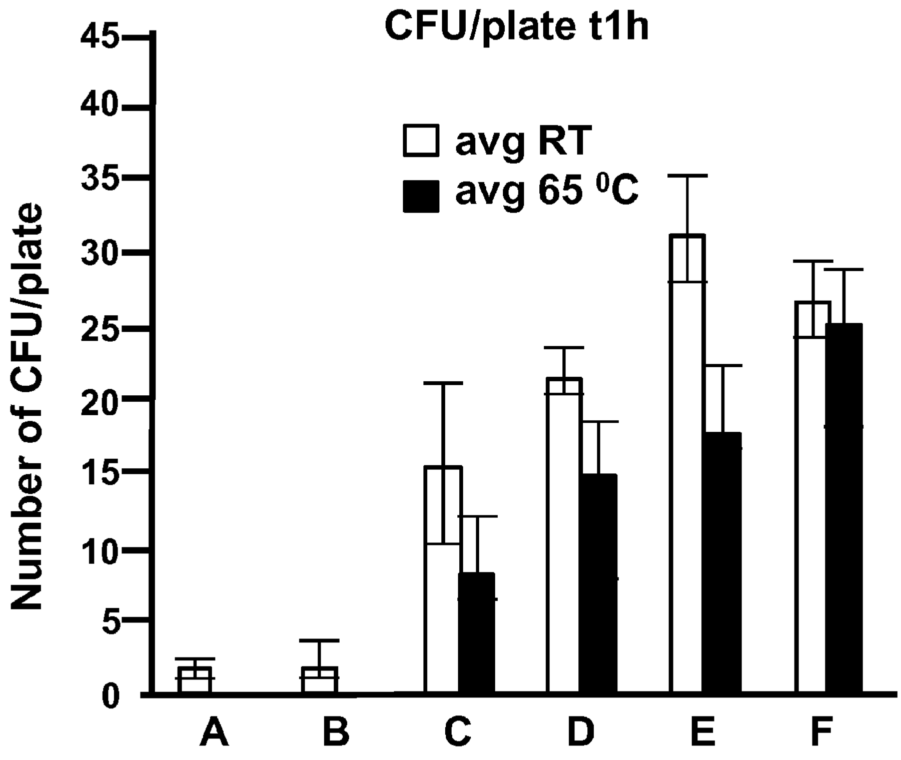
Figure 3C:
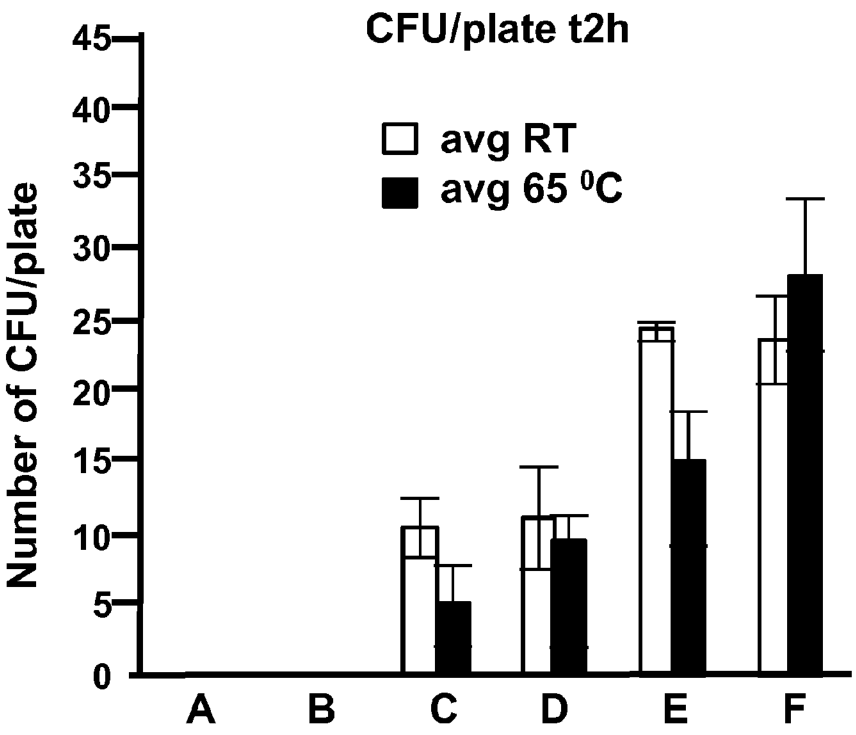
Figure 3D:
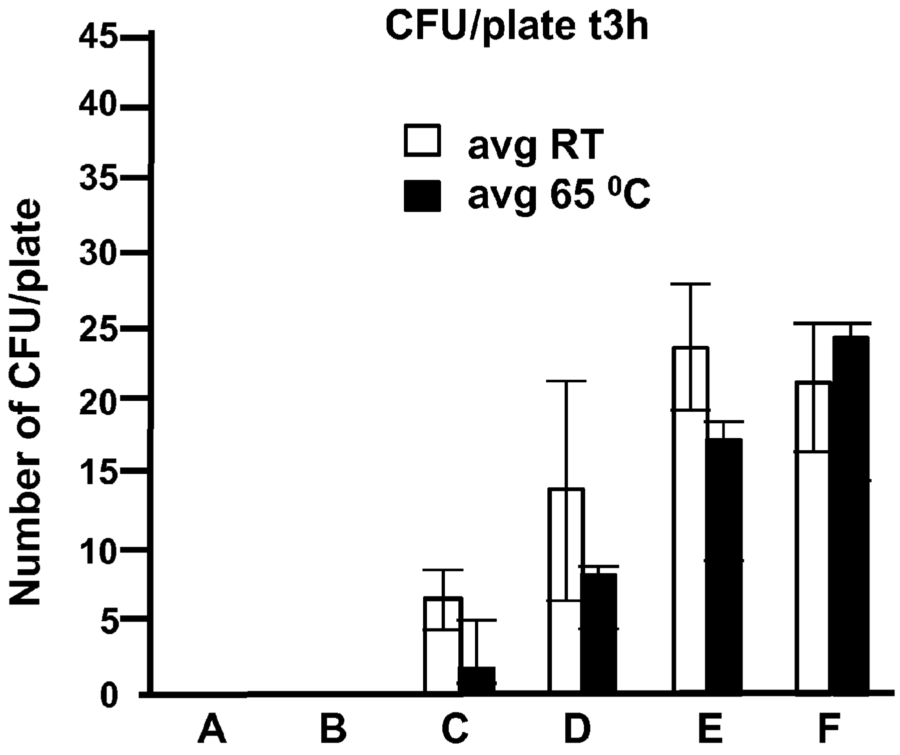
Figure 3E:
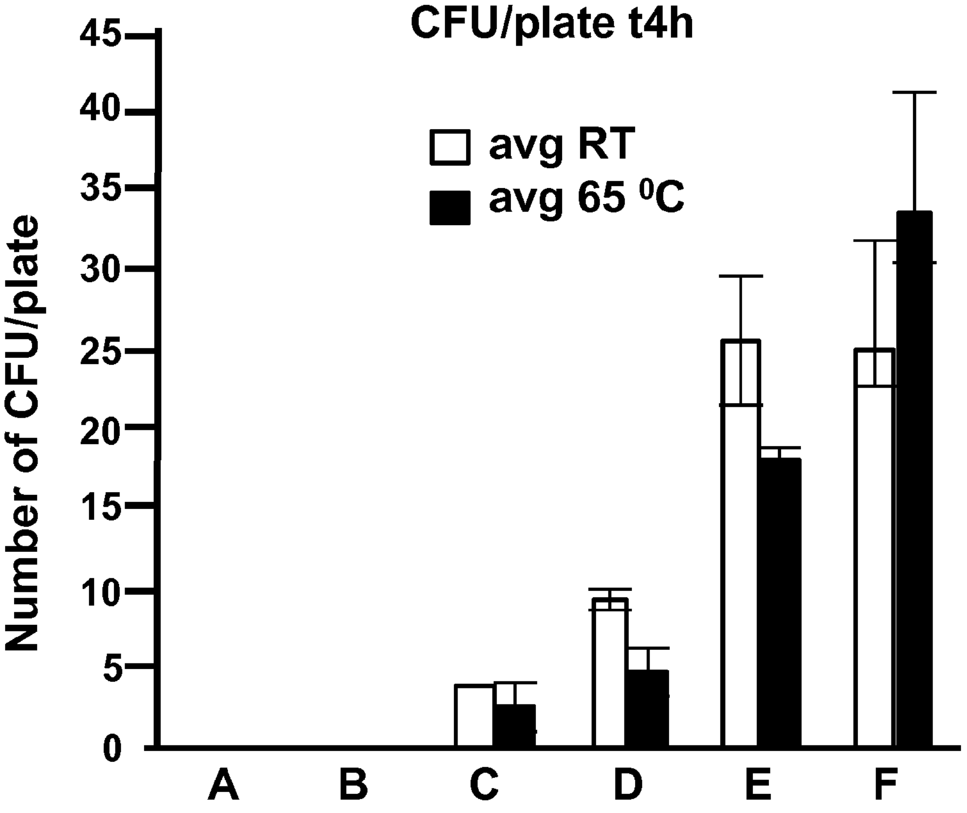

Experiment A3:

250 μl spore suspension ($5\times10^4$ spores) were added to 25 ml of the reagents. Sampling time points were t=0 (spores were added and after mixing with the reagent, 100 μl of the suspension were removed for enumeration), t=10 min, t=45 min, t=90 min, t=180 min. Average plate counts (FIGS. 1A-3E) are based on counting three plates; error bars indicate+/±one standard deviation.

Experiments A4, A5:

In experiment A4, 250 μl spore suspension ($5\times10^4$ spores) were added to 25 ml of the reagents. In experiment A5, 625 μl spore suspension ($1.25\times10^5$ spores) were added to 25 ml of the reagents. Sampling time points were t=0, t=1 h, t=2 h, t=3 h, t=4 h, t=5 h. To differentiate whether CFU originated from vegetative cells or from spores, at each time point samples were split in two equivalent aliquots. One aliquot was subjected to heat treatment (65° C., 30 min) to kill vegetative cells before enumeration of residual heat-resistant spores. The other aliquot was plated at room temperature (RT). Average plate counts (FIGS. 2A-2E and 3A-3E, respectively) are based on counting three plates; error bars indicate+/−one standard deviation.

Experiment A3:

At t=45 min recovery of CFUs from flasks A and B was reduced to 9% (1.7 CFU) and 43% (8 CFU), respectively, as compared to control flask F. At t=90 min and t=180 min, zero colony forming units (CFU) were recovered from flasks A and B. For flasks C and D retrieval decreased over time but did not drop below 16% (reagent C) and 39% (reagent D) at 180 min. Recovery levels from the flask with reagent E did not decrease (Table 16).

TABLE 16

Experiment A3: CFU % recovery (as compared to control flask F)

| | 0 min | 10 min | 45 min | 90 min | 180 min |
|---|---|---|---|---|---|
| A | 85 | 81 | 9 | 0 | 0 |
| B | 121 | 66 | 43 | 0 | 0 |
| C | 142 | 77 | 82 | 48 | 16 |
| D | 108 | 81 | 55 | 64 | 39 |
| E | 119 | 65 | 94 | 144 | 95 |
| F | 100 | 100 | 100 | 100 | 100 |

Experiments A4, A5:

In both experiments CFU recovery from flasks A and B at t=0 and t=1 h originated from heat-sensitive cells because colony counts were zero for the samples which received heat treatment. No CFU were retrieved from flask A or B for t=2 h, t=3 h, t=4 h (FIGS. 2A-2E and 3A-3E). For both reagents C and D % recovery decreased over time but of all compounds tested reagents A and B killed most effectively (Tables 17-20). Reagent E was not more effective than the water control F (FIGS. 2A-2E and 3A-3E).

TABLE 17

| Experiment A4 absent heat: CFU % recovery (as compared to control flask F): RT | | | | | |
|---|---|---|---|---|---|
| | 0 min | 1 h | 2 h | 3 h | 4 h |
| A | 81 | 2 | 0 | 0 | 0 |
| B | 85 | 12 | 0 | 0 | 0 |
| C | 81 | 71 | 33 | 23 | 15 |
| D | 89 | 54 | 27 | 30 | 15 |
| E | 85 | 90 | 87 | 98 | 79 |
| F | 100 | 100 | 100 | 100 | 100 |

TABLE 18

| Experiment A4 with heat: CFU % recovery (as compared to control flask F): 65° C. | | | | | |
|---|---|---|---|---|---|
| | 0 min | 1 h | 2 h | 3 h | 4 h |
| A | 0 | 0 | 0 | 0 | 0 |
| B | 0 | 0 | 0 | 0 | 0 |
| C | 27 | 13 | 6 | 8 | 0 |
| D | 70 | 78 | 45 | 33 | 46 |
| E | 48 | 53 | 74 | 68 | 114 |
| F | 100 | 100 | 100 | 100 | 100 |

TABLE 19

| Experiment A5 absent heat: CFU % recovery (as compared to control flask F): RT | | | | | |
|---|---|---|---|---|---|
| | 0 min | 1 h | 2 h | 3 h | 4 h |
| A | 128 | 6 | 0 | 0 | 0 |
| B | 124 | 6 | 0 | 0 | 0 |
| C | 97 | 58 | 44 | 32 | 16 |
| D | 105 | 80 | 46 | 67 | 37 |
| E | 122 | 117 | 103 | 113 | 103 |
| F | 100 | 100 | 100 | 100 | 100 |

TABLE 20

| Experiment A5 with heat: CFU % recovery (as compared to control flask F): 65° C. | | | | | |
|---|---|---|---|---|---|
| | 0 min | 1 h | 2 h | 3 h | 4 h |
| A | 0 | 0 | 0 | 0 | 0 |
| B | 0 | 0 | 0 | 0 | 0 |
| C | 58 | 32 | 18 | 8 | 8 |
| D | 75 | 58 | 34 | 34 | 14 |
| E | 71 | 69 | 53 | 71 | 54 |
| F | 100 | 100 | 100 | 100 | 100 |

While reagents C and D in a 4-hour time frame had a negative effect on spore survival, neither one of these reagents was as effective in killing spores as reagents A and B. Reagent E was not different from the water control F.

Viable cell counts demonstrated that reagents A and B affected heat sensitivity of spores very quickly at the t=0 time point suggesting induction of a break in spore dormancy. Chemical disinfectants which are not toxic and able to diminish resistance of spores to killing are potentially of great benefit.

Example 8

Efficacy of Compositions to Treat Contaminated Seeds

Since 1994, raw sprouts have been implicated as vehicles of outbreaks of *E. coli* O157:H7 and *Salmonella* both nationally and internationally. Most outbreaks were associated with alfalfa sprouts, but cress, mung bean, and clover sprouts have been implicated. Many treatments, including the use of heat and/or chemicals (e.g., NaOCl, $Ca(OCl)_2$, acidified $NaClO_2$, LiOCl, detergents, acidified $ClO_2$, $Na_3PO_4$, acidic calcium sulfate, and $H_2O_2$) have been evaluated for their ability to reduce *E. coli* O157:H7 contamination on alfalfa seeds. However none of these treatments can definitely eliminate the pathogen and render seeds with acceptable germination rates. Accordingly, applicants have investigated the ability of monoprotic acids/surfactant compositions as a wash solutions for eliminating *E. coli* O157:H7 and *Salmonella* from seeds, while retaining acceptable germination rates.

A 5-strain mixture of *E. coli* O157:H7 or *S. Typhimurium* at $10^8$ CFU/g was inoculated on alfalfa seeds. The seeds were dried at 21° C. for up to 72 h. A 0.5% levulinic acid and 0.05% SDS treatment for 5 min at 21° C. reduced *E. coli* O157:H7 and *S. Typhimurium* populations to undetectable levels (<5 CFU/g), however, some treated seeds were pathogen-positive by selective enrichment culture.

Bacterial Strains.

To facilitate enumeration of *E. coli* O157:H7, nalidixic acid-resistant (50 μg/ml) strains were used. Five isolates of *Escherichia coli* O157:H7, including 932 (human isolate), E009 (beef isolate), E0018 (cattle isolate), E0122 (cattle isolate), E0139 (deer jerky isolate) or five isolates of *Salmonella typhimurium* DT104, including H2662 (cattle isolate), 11942A (cattle isolate), 13068A (cattle isolate), 152N17-1 (dairy isolate) and H3279 (human isolate) were used as 5-strain composite mixtures.

Chemicals and Chemical Treatments.

Levulinic acid at 0.5% and 0.05% and sodium dodecyl sulfate (SDS) were tested in combination at 21° C.±2° C. as a wash treatment for their killing effect on *E. coli* O157:H7 and *S. typhimurium* on alfalfa seeds. Calcium hypochlorite (20,000 μg/ml (ppm)) was used as a positive control and deionized water was used as a negative control.

Deionized, unchlorinated water (filter sterilized through a 0.2-μm regenerated cellulose filter), tap water and autoclaved tap water were used.

Inoculation of alfalfa seeds. Alfalfa seeds were obtained from Caudill Seeds Co., Louisville, Ky., and had a germination rate of approximately 91%. Dry seeds (50 g) were placed in a sterilized glass beaker (1 L) and 5 ml of a 5-strain mixture of *E. coli* O157:H7 or *S. Typhimurium* DT 104 ($10^8$-$10^9$ CFU/ml or $10^3$-$10^4$ CFU/ml) was inoculated on the surface of the seeds then dried in a laminar flow hood for 1, 4, 24, 48, and 72 h.

Example 9

Determination of *Salmonella* and *E. Coli* O157:H7 Inactivation on Alfalfa Seeds Inoculated and dried alfalfa seeds (50-g samples) were placed in a 1000-ml glass beakers containing 200 ml of levulinic acid plus SDS or controls and agitated at 150 rpm with a magnetic stir bar at 21° C. for 0, 1, 2, 5, 10, 20, 30 and 60 min. Following treatment, the sample (1 or 25 seeds per gm or ml) was placed in a stomacher bag containing 9 ml or 25 ml of 0.1 M phosphate buffer, pH 7.2 (PBS), or neutralizing buffer, and pummeled for 1 minute at 150 rpm in a stomacher blender. The suspension was serially (1:10) diluted in 0.1% peptone water and 0.1 ml of each dilution was surface-plated in duplicate onto plates of TSA and Sorbitol MacConkey agar each containing 50 μg nalidixic acid/ml (TSA-NA and SMA-NA) for *E. coli* O157:H7; and TSA and XLD containing ampicillin (32 μg/ml), tetracycline (16 μg/ml) and streptomycin (64 μg/ml) (TSA+ and XLD+) for *S. typhimurium* DT 104. All plates were incubated at 37° C. for 48 h.

Determination of Seed Germination Percentage.

To determine the germination percentage, treated and control seeds (5 gram per replicate) were placed on the surface of a plastic tray. A second tray containing 200 ml of sterile deionized water was placed with tray with seeds and water dropped into lower tray to maintain uniform moisture. The seeds were incubated at approximately 22° C. for 72 h.

Results and Discussions:

A viable population of $10^8$ CFU *E. coli* O157:H7/g of alfalfa seeds was present after drying for 4 h, as shown in Table 21.

TABLE 21

*E. coli* O157:H7 counts on alfalfa seeds inoculated with $10^8$ CFU/g and dried at 21° C.

| Treatment method | *E. coli* O157:H7 counts (CFU/g) on seeds dried for: | | | | | | | |
|---|---|---|---|---|---|---|---|---|
| | 4 h | | | | | | | |
| Mins of exposure | 0$^a$ | 1 | 2 | 5 | 10 | 20 | 30 | 60 |
| 0.1M PBS, pH 7.2 | 8.1 | 8.2 | 8.2 | 8.1 | 8.2 | 8.3 | 8.3 | 8.1 |
| 20,000 ppm, $Ca(OCl)_2$, pH 11.4 | +$^b$ | + | –$^c$ | + | 1.7 | 2.0 | 1.7 | + |
| 0.5% levulinic acid + 0.05% SDS, pH 3.2 | 1.7 | 2.7 | 3.0 | 2.5 | 2.8 | 2.0 | 2.6 | 2.2 |
| | 24 h | | | | | | | |
| Mins of exposure | 0 | 1 | 2 | 5 | 10 | 20 | 30 | 60 |
| 0.1M PBS, pH 7.2 | 4.7 | 4.8 | 4.9 | 5.0 | 4.7 | 4.9 | 4.8 | 4.9 |
| 20,000 ppm, $Ca(OCl)_2$, pH 11.4 | + | – | – | – | – | – | – | + |
| 0.5% levulinic acid + 0.05% SDS, pH 3.2 | 1.7 | 1.4 | 0.7 | + | + | + | – | + |
| | 48 h | | | | | | | |
| Mins of exposure | 0 | 1 | 2 | 5 | 10 | 20 | 30 | 60 |
| 0.1M PBS, pH 7.2 | 4.0 | 4.1 | 4.0 | 4.1 | 4.1 | 4.0 | 4.0 | 3.9 |
| 20,000 ppm, $Ca(OCl)_2$, pH 11.4 | + | – | + | – | – | – | – | – |
| 0.5% levulinic acid + 0.05% SDS, pH 3.2 | 2.7 | 2.1 | + | + | + | + | + | + |
| | 72 h | | | | | | | |
| Mins of exposure | 0 | 1 | 2 | 5 | 10 | 20 | 30 | 60 |
| 0.1M PBS, pH 7.2 | 3.8 | 3.9 | 3.9 | 4.0 | 4.0 | 4.1 | 4.0 | 4.1 |
| 20,000 ppm, $Ca(OCl)_2$, pH 11.4 | + | + | + | – | + | + | – | – |
| 0.5% levulinic acid + 0.05% SDS, pH 3.2 | 1.9 | 1.4 | 1.1 | + | + | – | – | + |

$^a$The actual time 0 was delayed by 20 to 30 seconds due to time for sample processing.

$^b$+, Below the minimum detection level by direct plating (<1.7 log CFU/ml), but positive by enrichment culture.

$^c$–, Negative by direct plating and enrichment culture.

Treatments with 20,000 ppm calcium hypochlorite or 0.5% levulinic acid plus 0.05% SDS for up to 60 min reduced the *E. coli* O157:H7 population by greater than 6 and 5 log CFU/g, respectively.

The population of *E. coli* O157:H7 was reduced by 3 log CFU/g after drying for 24 h. Treatment with calcium hypochlorite and 0.5% levulinic acid plus 0.05% SDS for 5 min reduced *E. coli* O157:H7 populations to levels only detectable by enrichment culture. Similar results were observed with seeds dried for 48 and 72 h, as shown in Table 21.

A viable population of $10^6$ to $10^7$ CFU *S. Typhimurium* DT 104/g of alfalfa seeds was present after drying for 4 h. Treatments with 20,000 ppm calcium hypochlorite or 0.5% levulinic acid plus 0.05% SDS provided similar results, inactivating all *Salmonella*, including by enrichment culture, within 5 min, as shown in Table 22.

TABLE 22

*S. typhimurium* DT 104 counts on alfalfa seeds inoculated with $10^8$ CFU/g and dried at 21° C.

| Treatment method | *S. typhimurium* DT 104 counts (CFU/g) on seeds dried for | | | | | | | |
|---|---|---|---|---|---|---|---|---|
| | 4 h | | | | | | | |
| Min of exposure | 0$^a$ | 1 | 2 | 5 | 10 | 20 | 30 | 60 |
| 0.1M PBS, pH 7.2 | 6.4 | 6.8 | 6.3 | 6.4 | 6.6 | 6.3 | 6.3 | 6.0 |
| 20,000 ppm, $Ca(OCl)_2$, pH 11.4 | +$^b$ | –$^c$ | – | – | – | – | – | – |
| 0.5% levulinic acid + 0.05% SDS, pH 3.2 | 3.1 | + | + | – | – | – | – | |
| | 24 h | | | | | | | |
| Min of exposure | 0 | 1 | 2 | 5 | 10 | 20 | 30 | 60 |
| 0.1M PBS, pH 7.2 | 4.4 | 4.2 | 4.3 | 4.4 | 4.5 | 4.6 | 4.6 | 4.3 |
| 20,000 ppm, $Ca(OCl)_2$, pH 11.4 | + | + | – | – | – | – | – | – |
| 0.5% levulinic acid + 0.05% SDS, pH 3.2 | 1.6 | 2.4 | 1.2 | + | + | – | – | – |
| | 48 h | | | | | | | |
| Min of exposure | 0 | 1 | 2 | 5 | 10 | 20 | 30 | 60 |
| 0.1M PBS, pH 7.2 | 4.0 | 4.1 | 4.2 | 4.3 | 4.2 | 4.4 | 4.4 | 4.3 |
| 20,000 ppm, $Ca(OCl)_2$, pH 11.4 | + | + | – | – | + | – | – | – |
| 0.5% levulinic acid + 0.05% SDS, pH 3.2 | 3.0 | + | – | – | + | – | + | – |
| | 72 h | | | | | | | |
| Min of exposure | 0 | 1 | 2 | 5 | 10 | 20 | 30 | 60 |
| 0.1M PBS, pH 7.2 | 4.0 | 4.0 | 3.9 | 4.1 | 4.1 | 4.5 | 4.1 | 4.2 |
| 20,000 ppm, $Ca(OCl)_2$, pH 11.4 | – | – | – | – | – | + | + | – |
| 0.5% levulinic acid + 0.05% SDS, pH 3.2 | 2.3 | + | + | + | – | – | + | + |

$^a$The actual time 0 was delayed by 20 to 30 seconds due to time for sample processing.

$^b$+, Below the minimum detection level by direct plating (<1.7 log CFU/ml), but positive by enrichment culture.

$^c$–, Negative by direct plating and enrichment culture.

Drying seeds for 24 h, 48 h, or 72 h reduced the population of *Salmonella* by ca. 4 log CFU/g. Treatment with 20,000 ppm calcium hypochlorite or 0.5% levulinic acid plus 0.05% SDS for 5 min reduced *Salmonella* to levels undetectable by direct plating, but still detectable by enrichment culture (Table 22).

Both chemical treatment solutions were negative for *E. coli* O157:H7 or *Salmonella* following treatment of contaminated seeds. Seeds treated for 10 min were transferred to a stomacher bag and pummeled for another 10 min at 200 rpm. Results revealed that all five samples treated with 20,000 ppm calcium hypochlorite or 0.5% levulinic acid and 0.05% SDS were *E. coli* O157:H7- and *Salmonella*-negative by direct plating, whereas two of ten samples treated with 0.5% levulinic acid and 0.05% SDS were negative by enrichment culture.

The germination rate of alfalfa seed treated with 0.5% levulinic acid plus 0.05% SDS for 1 hour at 21° C. was 80%, with tap water was 71%, and for 20,000 ppm calcium hypochlorite was 47.3%.

Similar results of *E. coli* O157:H7 and *Salmonella* inactivation on alfalfa seeds were obtained with treatments of 20,000 ppm calcium hypochlorite, pH 11.4, or 0.5% levulinic acid plus 0.05% SDS, pH 3.2. Alfalfa seed germination percentages were substantially greater when treated with levulinic acid plus SDS relative to treatments using calcium hypochlorite.

Example 10

The Determination of Shelf-Life of Treated Lettuce

Whole Romaine lettuce (3 heads in each bag) was soaked in a plastic container with 5 liters of solution composed of 0.5% levulinic acid plus 0.05% SDS, pH 2.9 at 21° C. for either 15 or 30 min, then rinsed in same amount of tap water for 3 times. The samples of treated lettuce (inner and outer leaves) were kept in a layer of paper towel and dried in a laminar hood for 30 min for removing extra water. Then, the lettuce was kept in the original bag at 5° C. The lettuce treated with tap water only was used as the negative control.

Results indicated that the color, shape, and fragility of lettuce treated with 0.5% levulinic acid plus 0.05% SDS for either 15 or 30 min was the same in 20 days when compared with lettuce treated with water only. At 30 days, these characteristics, including color, shape, and fragility were better when compared with lettuce treated with water, which showed evidence of bacteria- and/or fungi-induced decay of the surface of lettuce leaves.

Example 11

Reduction of *E. Coli* O157:H7 and *Salmonella* on Meat

The goal of this experiment is to develop and validate a practical treatment to eliminate or reduce bacterial, including *E. coli* O157:H7 and *Salmonella* contamination, on the surface of processed meat.

Phase 1 of the experiments would determine the relationship between different chemical concentrations and rinse exposure time at 5° C. on the inactivation of *E. coli* O157:H7 or *Salmonella* on beef trimming pieces. A 5-strain mixture of *E. coli* O157:H7 or *Salmonella*, including Typhimurium DT 104 was used. Beef trimmings were into about 2-in cubes. Two inoculation levels (high inoculum at $10^5$ CFU/g and low inoculum at $10^2$ CFU/g) were used. Following inoculation, the meat pieces (45 in each group) were held at 5° C. for 1 h, 2 h, 4 h, or 24 h for pathogen attachment and acclimation.

Three treatment methods (levulinic acid+SDS, acidified sodium chlorite, and water only) were compared for antimicrobial activity. The concentration of levulinic acid ranged from about 0.5 to about 3.0% and of SDS from about 0.05 to about 2.0%, and treatments were applied at 5° C. for 1 min, 2 min, 3 min, 4 min, and 5 min. Each meat piece was treated in a stomacher bag, then removed to another bag containing 0.1 M phosphate-buffer or neutralizing buffer to stop further chemical activity. All treatment and washing solutions were assayed for either *E. coli* O157:H7 or *Salmonella* and aerobic plate counts (APC).

Phase 2 of the experiment was to evaluate whether *E. coli* O157:H7 or *Salmonella* could be recovered from ground beef prepared from levulinic acid+SDS-treated beef trim and stored frozen for up to 6 months. The concentration of levulinic acid+SDS and exposure time at 5° C. used was based on the data obtained from the Phase 1 studies. Beef trim treated by the three methods described for the Phase 1 study was ground, formed into patties, packaged and frozen at −20° C. for up to 6 months. Beef patties were assayed monthly for either *E. coli* O157:H7 or *Salmonella* and APC.

Phase 3 of the experiment validated advantageous levulinic acid and SDS concentrations and exposure time to treat beef trim and confirm, under storage conditions, the inactivation of *E. coli* O157:H7 and *Salmonella* in ground beef made from the treated beef trim. Beef was cut into about 2-in cubes and a volume of 1.0-ml of bacterial solution containing approximately $10^4$ CFU *E. coli* O157:H7 or *S. Typhimurium* DT 104 was inoculated on the surface. The beef cubes were mixed, held at 5° C. for 3 h, and then treated with levulinic acid and SDS at concentrations and an exposure time determined in the Phase 1 and 2 studies. After treatment, the beef cubes were ground as a mixture. The ground meat was packaged, frozen, stored at −20° C. for up to 3 months, and assayed periodically for *E. coli* O157:H7 or *Salmonella* and APC.

Example 12

Previous studies have revealed that the surface temperature of beef cuts is critical (the meat has to be in soft condition) and the chemical solution and its bactericidal effect on meat are stable and active between 8° C. to 21° C. Studies also addressed the effect of levulinic acid plus SDS on pathogens on beef at 12° C.±2° C. with the treatment solution at 21° C.

Beef portions were cut into about 0.3×2.5×6 in. pieces weighing from about 400 to about 750 g. A piece of meat at 5° C. was soaked in 500 ml containing either *E. coli* O157:H7 or *S. typhimurium* suspension ($10^{5-6}$ CFU/ml) for 1 min, and this contaminated sample was contacted for 2 min with 10 other pieces of beef to simulate cross-contamination that might occur during processing. After inoculation the beef pieces were held in a laminar flow hood for 30 min. The surface temperature on the beef cuts ranged from about 10° C. to about 12° C. and they were malleable to the touch. Five randomly selected meat samples were individually treated for 30 secs in Whirl Pak bags each containing 100 ml 3% levulinic acid plus 2% SDS (treated) or 100 ml of water (control) with hand massaging. Each sample was removed and transferred into another Whirl Pak bag containing 20 ml 0.1 M PBS for the treated beef or 20 ml of water for water-treated samples.

*E. coli* O157:H7 and *Salmonella* counts on the beef treated with 3% levulinic acid and 2% SDS were less than 0.7 log CFU/sample and *E. coli* O157:H7 and *Salmonella* counts on beef treated with water only were 3.0 CFU log CFU/sample.

These results confirmed that surface temperature was significant for levulinic acid plus SDS inactivation (chemical inactivation) of either *E. coli* O157:H7 or *Salmonella* on meat surfaces.

Example 13

Reduction of *E. Coli* O157:H7 and *Salmonella* in Ground Beef

The antimicrobial properties of 0.5% levulinic acid and 0.05% sodium dodecyl sulfate (SDS) plus other organic acid and detergent combinations were initially evaluated with a pure culture of *E. coli* O157:H7, as shown in Table 23.

TABLE 23

Reduction of *E. coli* O157:H7 by acids and antimicrobials or SDS at 21° C.

| Chemical treatment | *E. coli* O157 counts (log CFU/ml) at min: 0[a] | 1 | 2 | 5 | 10 | 20 | 30 | 60 |
|---|---|---|---|---|---|---|---|---|
| *E. coli* O157:H7 only (Control) | 7.7 | 7.6 | 7.7 | 7.7 | 7.8 | 7.7 | 7.8 | 7.7 |
| 0.5% adipic acid + 0.05% benzalkonium chloride (pH 3.1) | 2.7 | 1.7 | +[b] | –[c] | – | – | – | – |
| 0.5% cetylpyidinum chloride + 0.05% SDS (pH 5.8) | + | + | + | + | + | + | + | + |
| 0.5% citric acid + 0.05% SDS (pH 2.5) | – | – | – | – | – | – | – | – |
| 0.5% ethylenediaminetetraacetic acid + 0.05% SDS (pH 3.0) | – | – | – | – | – | – | – | – |
| 0.5% eugenol + 0.05% SDS (pH 2.6) | – | – | – | – | – | – | – | – |
| 0.5% fumaric acid + 0.05% SDS (pH 2.4) | + | – | – | – | – | – | – | – |
| 0.5% hexaoic acid + 0.05% SDS (pH 3.2) | 2.7 | 1.7 | – | – | – | – | – | – |
| 0.5% levulinic acid + 0.05% benzalkonium chloride (pH 3.1) | – | – | – | – | – | – | – | – |
| 0.5% levulinic acid + 0.05% cetypridinium chloride (pH 3.1) | – | – | – | – | – | – | – | – |
| 0.5% levulinic acid + 0.05% cocamide MEA (pH 3.1) | >5.3 | >5.3 | >5.3 | >5.3 | >5.3 | >5.3 | >5.3 | >5.3 |
| 0.5% malic acid + 0.05% SDS (pH 2.6) | + | + | – | – | – | – | – | – |
| 0.5% phosphoric acid + 0.05% SDS (pH 1.7) | – | – | – | – | – | – | – | – |
| 0.5% succinic acid + 0.05% SDS (pH 2.9) | – | – | – | – | – | – | – | – |
| 0.5% tartaric acid + 0.05% SDS (pH 2.5) | + | + | + | – | – | – | – | – |

[a]The actual time 0 was delayed by 5 to 10 seconds due to time for sample processing.
[b]+, *E. coli* O157:H7-positive by enrichment culture but not by direct plating (minimum detection level is 0.7 log CFU/ml).
[c]–, *E. coli* O157:H7-negative by direct plating and enrichment culture.

Results revealed that the levulinic acid+SDS combination was, within 1 minute, among the most effective of the antimicrobials evaluated. In addition, the solution of levulinic acid plus SDS was clear and stable at temperatures ranging from about 8° C. to about 21° C. and the antimicrobial activity did not change after holding this preparation at room temperature (20° C.-24° C.) for 60 days. The preparation at the highest concentrations (3% levulinic acid plus 2% SDS) precipitated when held at 5° C. for 24 h. The precipitated solution redissolved when it was warmed to room temperature, and this condition did not affect its antimicrobial activity.

Example 14

Studies to assess the effect of SDS on the emulsification of fat in further processed meat products revealed a high concentration of levulinic acid at 3% plus 2% SDS did not affect color or visual appearance of fat when held at 21° C. for up to 20 mins.

The antimicrobial efficacy of 3% levulinic acid plus 2% SDS at 8° C. against *E. coli* O157:H7 on beef cuts without and with fat (20-30%) at 5° C. was determined. *E. coli* O157:H7 was not enumerated on meat samples without fat so quantitative results were not obtained for this study. The pathogen did not survive in the treatment solution after the treatment was applied but was detected on treated meat cuts, as shown in Table 24.

TABLE 24

Activity of 3% levulinic acid + 2% SDS at 8° C. against *E. coli* O157:H7 on beef

| Time (min) | *E. coli* O157:H7 count (log CFU/$cm^2$ or ml): Meat treated with water only | Meat treated with chemical solution | Chemical solution after treating meat |
|---|---|---|---|
| 1 | 5.9 | +[a] | –[b] |
| 2 | 5.9 | + | – |
| 3 | 5.8 | + | – |
| 5 | 5.8 | + | – |
| 10 | 5.8 | + | – |
| 20 | 5.6 | + | – |
| 30 | 5.6 | + | – |
| 60 | 5.8 | + | – |

[a]+, Enrichment culture was *E. coli* O157-positive (did not enumerate by direct plating).
[b]–, Enrichment culture was *E. coli* O157-negative.

*E. coli* O157 counts were reduced by about 1.5 log within 1-5 minutes of 3% levulinic acid plus 2% SDS exposure on beef cuts with fat contents ranging from 25-35% at 5° C., as shown in Table 25. Meat at 5° C. treated with the 3% levulinic acid plus 2% SDS solution at 8° C., 21° C. or 37° C. yielded similar results (Table 25), hence temperature of the treatment solution between 8° C. and 37° C. had little influence on *E. coli* O157 inactivation if the meat temperature was held at 5° C. The treatment solutions following meat treatment were assayed for *E. coli* O157:H7 and results revealed that all treatment solutions were *E. coli* O157:H7-negative.

TABLE 25

| Activity of 3% levulinic acid + 2% SDS against *E. coli* O157:H7 on beef | | | | | | |
|---|---|---|---|---|---|---|
| | | *E. coli* O157:H7 count (log CFU/$cm^2$ or ml) | | | | |
| Time (min) | Meat weight (g) | Treat with water only at 8 ° C. | Treat chemical solution at 8° C. | Treat with chemical solution at 21° C. | Treat with chemical solution at 37° C. | Chemical solution after treatment |
| 1 | 447 | | 5.6 | | | –* |
| 3 | 491 | | 5.0 | | | – |
| 5 | 412 | | 4.9 | | | – |
| 1 | 535 | | | 5.4 | | – |
| 3 | 534 | | | 5.0 | | – |
| 5 | 617 | | | 5.1 | | – |
| 1 | 386 | | | | 5.4 | – |
| 3 | 551 | | | | 5.1 | – |
| 5 | 405 | | | | 5.2 | – |
| 5 | 381 (control) | 6.7 | | | | |

*–, Enrichment culture was *E. coli* O157-negative.

Because the surfaces of the beef cuts were rigid at 5° C. and layers between fat and muscle could not be stretched flat, treatment bags were hand massaged to provide better contact of the meat surfaces with the chemical solutions. Results revealed that a light hand massage increased the removal or inactivation of *E. coli* O157:H7 on beef at 5° C. treated with 3% levulinic acid plus 2% SDS at 8° C. by an additional 1 log, as shown in Table 26.

TABLE 26

| Activity of 3% levulinic acid + 2% SDS at 8° C. on *E. coli* O157:H7 on beef (25-35% fat content) at 5° C. with intermittent hand-massage. | | | |
|---|---|---|---|
| | *E. coli* O157:H7 count (log CFU/$cm^2$ or ml) | | |
| Time (min) (meat weight; gm) | Meat treated with water only | Meat treated with chemical solution | Chemical solution after treating meat |
| 1 (506) | | 3.9 | –* |
| 2 (530) | | 4.9 | – |
| 3 (359) | | 4.8 | – |
| 5 (319) | | 4.4 | – |
| 5 (264) | 6.3 | | |

*–, Enrichment culture was *E. coli* O157-negative.

The relationship between treatment solutions at different temperatures and meat at 5° C. in killing/removal of *E. coli* O157:H7 on beef was determined. Holding chemical solutions at 8° C. and meat at 5° C. for 1 min, 2 min, and 5 min reduced *E. coli* O157:H7 populations by 1.4 to 2.4 log CFU/$cm^2$ (Table 26). All treatment solutions following treatment of meat were *E. coli* O157:H7-negative.

Example 15

The effect of increasing the temperature of the treatment solution on *E. coli* O157:H7 on beef at 5° C. was determined. The chemical solution of 3% levulinic acid plus 2% SDS at 21° C., 62° C. or 81° C. and contact time of 30 sec, 60 sec, and 90 sec reduced, *E. coli* O157:H7 counts in beef at 5° C. by 1 to 2 log/$cm^2$, with greater reduction at 81° C., as shown in Table 27. The surface color of treated beef at the higher temperatures (62° C. and 81° C.) for all contact times (30 sec, 60 sec and 90 sec) changed. Chemical solutions after treatment of beef were *E. coli* O157:H7-negative (Table 27).

TABLE 27

| Activity of 3% levulinic acid + 2% SDS on *E. coli* O157:H7 on beef (25-35% fat content; 4 × 4 × 3 in) at 5° C. | | | | | | |
|---|---|---|---|---|---|---|
| | | *E. coli* O157:H7 count (log CFU/$cm^2$ or ml) | | | | |
| Time (sec) | Meat weight (g) | Treat with water only at 8° C. | Treat with chemical solution at 21° C. | Treat with chemical solution at 62° C. | Treat with chemical solution at 81° C. | Chemical solution after treating meat |
| 30 | 272 | | 5.8 | | | –* |
| 60 | 296 | | 5.4 | | | – |
| 90 | 323 | | 5.7 | | | – |
| 30 | 447 | | | 5.7 | | – |
| 60 | 427 | | | 5.6 | | – |
| 90 | 437 | | | 5.5 | | – |
| 30 | 397 | | | | 5.4 | – |
| 60 | 371 | | | | 4.8 | – |
| 90 | 369 | | | | 5.1 | – |
| 90 | 459 (control) | 6.8 | | | | |

*–, Enrichment culture was *E. coli* O157-negative.

Studies of beef cuts that were at 5° C. revealed the tissue was solid whereby the treatment solution likely could not completely contact *E. coli* O157:H7 attached to or embedded in the meat. Increasing the temperature of the meat to 12° C. and of the treatment solution to room temperature (21° C.) resulted in rapid inactivation of *E. coli* O157:H7 on the meat, decreasing from 5.8 log CFU/cm$^2$ to undetectable levels within 3 minutes (greater than a 5 log reduction; Table 28).

TABLE 28

Activity of 3% levulinic acid + 2% SDS at 21° C. on *E. coli* O157:H7 on beef (25-35% fat content; 4 × 4 × 3 inches) at 12° C. with intermittent hand-massaging.

| Time (min) (meat weight; gm) | *E. coli* O157:H7 count (log CFU/cm$^2$ or ml) Meat treated with water only | Meat treated with chemical solution | Chemical solution after treating meat |
|---|---|---|---|
| 1 (373) | | 5.5 | –* |
| 2 (370) | | 3.9 | – |
| 3 (296) | | <0.7 | – |
| 5 (242) | | <0.7 | – |
| 5 (355) | 5.8 | | |

*–, Enrichment culture was *E. coli* O157-negative.

The color of the treated meat was not changed within 5 min, and fat content of the meat did not appear to have a major influence on the antimicrobial activity of the levulinic acid plus SDS treatment on beef held at 12° C. Solution applied for 5 min on beef held at 8° C. or 12° C. reduced *E. coli* O157 populations by 3.3 (Table 29) and >5.0 log CFU/cm$^2$, respectively.

TABLE 29

Activity of 3% levulinic acid + 2% SDS at 12° C. on *E. coli* O157:H7on beef (25-35% fat content; 4×4×3 in) at 8° C. with agitation (150 rpm).

| Time (min) (meat weight; gm) | *E. coli* O157:H7 count (log CFU/cm$^2$ or ml) Meat treated with PBS only | Meat treated with chemical solution | Chemical solution after treating meat |
|---|---|---|---|
| 0 (281) | | 5.2 | –* |
| 1 (293) | | 4.2 | – |
| 3 (370) | | 4.1 | – |
| 5 (329) | | 3.3 | – |
| 1 (983, ground) | | 4.1 | |
| 5 (358) | 6.6 | | |

*–, Enrichment culture was *E. coli* O157-negative.

Meat at 8° C. was treated with 3% levulinic acid plus 2% SDS at 12° C. for 2 min then ground, formed into meat patties, and frozen at −25° C. Chemical treatment for 2 min reduced the *E. coli* O157:H7 population by 1 to 2 log CFU/g; grinding and freezing resulted in an additional approximately 1 log CFU *E. coli* O157/g reduction in beef (Table 30).

TABLE 30

Activity of 3% levulinic acid + 2% SDS (chemical solution) at 12° C. on *E. coli* O157:H7 on beef trimmings (25-35% fat content; 4×4×3 inches) at 8° C. with agitation (150 rpm).

| Time (min) (meat weight; gm) | *E. coli* O157:H7 count (log CFU/g or ml) Meat treated with PBS only | Meat treated with chemical solution | Chemical solution after treating meat |
|---|---|---|---|
| 2 (102) | | 4.6 | –* |
| 2 (48) | | 4.4 | – |
| 2 (68) | | 5.0 | – |
| 2 (118) | | 5.0 | – |
| 2 (114) | 6.5 | | |
| 5 (79) | 6.0 | | |
| 2 (102) | 5.9 | | |
| 2 (4900, ground) | 6.0 | | |
| 2 (5000, ground) | | 5.0 | |
| 2 (ground, week 1) | 5.0 | | |
| 2 (ground, week 1) | | 4.3 | |
| 2 (ground, week 2) | 5.4 | | |
| 2 (ground, week 2) | | 4.2 | |
| 2 (ground, week 3) | 4.7 | | |
| 2 (ground, week 3) | | 3.7 | |
| 2 (ground, week 4) | 4.4 | | |
| 2 (ground, week 4) | | 3.5 | |

*–, Enrichment culture was *E. coli* O157-negative.

A similar experiment using meat at 8° C. and 3% levulinic acid plus 2% SDS treatment solution at 8° C. was evaluated for inactivation of *Salmonella typhimurium* DT 104.

*S. typhimurium* DT 104 was more sensitive to the equivalent chemical treatment than *E. coli* O157:H7. *S. typhimurium* DT 104 populations on the meat were reduced by 2.1, 2.6, and greater than 5 log CFU/cm$^2$ for contact times of 1 min, 2 min, and 3 min, respectively. A strip of meat contaminated with *S. typhimurium* DT 104 at ca. 5 log CFU/cm$^2$ was mixed with another 5 strips of meat of similar size. The meat strips were divided into two groups. One group was treated with PBS and the other group was treated with 3% levulinic acid plus 0.05% SDS for 0.5 min. Following treatment, the meat strips were ground into beef patties and frozen at −25° C. The fate of *S. typhimurium* DT 104 in the patties was determined weekly. Results revealed that freezing reduced the *S. typhimurium* population by an additional 1 log CFU/g, as shown in Table 31.

TABLE 31

Activity of 3% levulinic acid + 2% SDS at 8° C. against *S. typhimurium* DT 104 on beef trimmings (25-35% fat content; 4×4×3 in) at 8° C. with hand massaging.

| Time (min) (meat weight; gm) | *S. typhimurium* DT 104 count (log CFU/cm$^2$, g, or ml) Meat treated with PBS only | Meat treated with chemical solution | Chemical solution after treating meat |
|---|---|---|---|
| 0 (368) | | 5.6 | –* |
| 1 (336) | | 3.6 | – |
| 2 (276) | | 3.1 | – |
| 3 (291) | | <0.7 (+) | – |
| 3 (321) | 5.7 | | |
| 5 (334) | | <0.7 (+) | – |
| 1 strip was contaminated with *S. typhimurium* DT104 and mixed with other strips | | | |
| 0.5 (5500, ground) | 4.9 | | |
| 0.5 (5500, ground) | | 3.9 | |
| 0.5 (ground, week 1) | 4.0 | | |
| 0.5 (ground, week 1) | | 2.9 | |

TABLE 31-continued

Activity of 3% levulinic acid + 2% SDS at 8° C. against *S. typhimurium* DT 104 on beef trimmings (25-35% fat content; 4×4×3 in) at 8° C. with hand massaging.

| Time (min) (meat weight; gm) | *S. typhimurium* DT 104 count (log CFU/$cm^2$, g, or ml) Meat treated with PBS only | Meat treated with chemical solution | Chemical solution after treating meat |
|---|---|---|---|
| 0.5 (ground, week 2) | 3.7 | | |
| 0.5 (ground, week 2) | | 3.0 | |
| 0.5 (ground, week 3) | 3.8 | | |
| 0.5 (ground, week 3) | | 2.8 | |
| 0.5 (ground, week 4) | 3.9 | | |
| 0.5 (ground, week 4) | | 3.0 | |

*–, Enrichment culture was *S. typhimurium* DT 104-negative.

Spray treatment of the beef (25-35% fat content) surface at 5° C. with different concentrations of levulinic acid plus SDS at 8° C. (with *E. coli* O157:H7 contamination on only one side and chemical treatment on only the same side) revealed only a small reduction (0.3-0.4 log with high chemical concentration, 10% levulinic acid plus 2% SDS) of *E. coli* O157:H7 (Table 32).

TABLE 32

*E. coli* O157:H7 counts on beef trimmings (25-35% fat content; 4×4×3 in) at 5° C. sprayed with solutions at 8° C. on one side of beef.

| Meat weight (g) | Solution | Spray times/ volume (ml) | Log CFU *E. coli* O157:H7/whole meat piece |
|---|---|---|---|
| 378 | 10% levulinic + | 5/3.7 | 2.8 |
| 380 | 2% SDS | | 2.8 |
| 278 | 5% levulinic + | 5/4.5 | 3.0 |
| 247 | 2% SDS | | 2.9 |
| 269 | 3% levulinic acid + | 5/4.1 | 3.1 |
| 239 | 2% SDS | | 2.9 |
| 214 | 0.5% levulinic acid + | 5/4.6 | 2.9 |
| 219 | 0.05% SDS | | 3.2 |
| 236 | 3% citric acid + | 5/4.6 | 3.0 |
| 206 | 2% SDS | | 3.2 |
| 181 | Tap water only | 5/3.1 | 3.1 |
| 163 | | 5/3.1 | 3.2 |
| 388 | Spray only* | 2/1.8 | 3.2 |

*Bacterial solution spray (2 times/1.8 ml)

The two-sided application of chemical treatments reduced *E. coli* O157:H7 populations by an additional 1 log CFU (Table 33) (meat color did not change and the high concentration of levulinic acid did not reduce the pH value of the meat).

TABLE 33

*E. coli* O157:H7 counts on beef trimming (45-55% fat content; 4×4× 3 in) at 5° C. after sprayed with different concentrations of chemical solutions at 8° C. on both sides of beef.

| Meat weight (g) | Chemical solution | Spray times/ volume (ml) | Log CFU *E. coli* O157:H7/ meat piece |
|---|---|---|---|
| 277 | 10% levulinic + | 10/7.4 | 1.7 |
| 272 | 2% SDS | | 1.8 |
| 271 | 5% levulinic + | 10/9 | 2.2 |
| 258 | 2% SDS | | 2.5 |
| 249 | 3% levulinic acid + | 10/8.2 | 2.5 |
| 234 | 2% SDS | | 2.1 |
| 229 | 0.5% levulinic acid + | 10/9.2 | 2.7 |
| 228 | 0.05% SDS | | 2.8 |
| 227 | 3% citric acid + | 10/9.2 | 2.2 |
| 223 | 2% SDS | | 2.2 |
| 399 | Tap water only | 10/6.2 | 2.9 |
| 363 | | 10/6.2 | 3.0 |
| 353 | | 10/6.2 | 2.8 |
| 198 | Spray only* | 2/1.8 | 2.8 |
| 186 | | 2/1.8 | 2.9 |

*Bacterial solution spray (2 times/1.8 ml)

It was concluded that (1) the chemical solution levulinic acid plus SDS was stable at temperatures ranging from 5° C. to 81° C.; (2) the surface of beef at 5° C. was rigid and this rigid condition appeared to minimize contact of chemical solution with the contaminating bacteria, thereby reducing antimicrobial efficacy; (3) the chemical treatment, even at a high acid concentration (10% levulinic acid) did not adversely affect meat color; (4) high-fat content of meat did not appear to reduce the antimicrobial efficacy of the chemical treatment; and (5) *S. typhimurium* DT 104 was more sensitive to the levulinic acid plus SDS chemical treatment than *E. coli* O157:H7.

Example 16

TABLE 34

Inactivation of *S. enteritidis* in a biofilm - chemical treatment applied as liquid at 21° C.

| Coupon material | Chemical solution | *Salmonella enteritidis* counts (log CFU/cm2) at minutes 0 | 1 | 2 | 5 | 10 | 20 |
|---|---|---|---|---|---|---|---|
| Stainless steel | PBS, pH 7.2 | 8.0 | 8.4 | 8.5 | 8.6 | 8.2 | 8.1 |
| | Acidified sodium chlorite (500 ppm), pH 2.8 | 7.5 | 5.9 | 5.7 | 5.4 | 6.2 | 6.0 |
| | 3% levulinic acid + 2% SDS, pH 3.0 | <0.7 | <0.7 | <0.7 | <0.7 | <0.7 | <0.7 |
| Polyvinyl chloride | PBS, pH 7.2 | 8.8 | 9.0 | 8.1 | 8.8 | 8.0 | 8.3 |
| | Acidified sodium chlorite (500 ppm), pH 2.8 | 6.9 | 5.5 | 5.8 | 5.3 | 4.2 | 2.9 |
| | 3% levulinic acid + 2% SDS, pH 3.0 | 2.3 | 1.7 | 2.0 | 2.2 | <0.7 | <0.7 |
| Glass | PBS, pH 7.2 | 8.2 | 8.7 | 8.4 | 8.4 | 8.4 | 8.4 |
| | Acidified sodium chlorite (500 ppm), pH 2.8 | 6.8 | 3.3 | 0.7 | 0.7 | <0.7 | <0.7 |
| | 3% levulinic acid + 2% SDS, pH 3.0 | <0.7 | <0.7 | <0.7 | <0.7 | <0.7 | <0.7 |

Example 17

TABLE 35

Inactivation of *S. enteritidis* in a biofilm - 3% levulinic acid plus 2% SDS applied as foam at 21° C.

| Coupon material | Chemical solution | *Salmonella Enteritidis* counts (log CFU/$cm^2$) at minutes 0 | 1 | 2 | 5 | 10 | 20 |
|---|---|---|---|---|---|---|---|
| Stainless | PBS, pH 7.2 | 7.3 | 7.7 | 8.0 | 7.2 | 8.0 | 7.3 |
| steel | 3% levulinic acid + 2% SDS, pH 2.8 | 8.3 | 6.7 | 6.8 | 4.0 | 2.3 | 2.0 |
| Polyvinyl | PBS, pH 7.2 | 8.0 | 8.3 | 8.2 | 8.6 | 8.2 | 8.6 |
| chloride | 3% levulinic acid + 2% SDS, pH 2.8 | 5.8 | 4.9 | 3.1 | 3.0 | 3.2 | 1.0 |
| Glass | PBS, pH 7.2 | 8.0 | 8.5 | 7.7 | 7.9 | 7.8 | 7.9 |
| | 3% levulinic acid + 2% SDS, pH 2.8 | 4.9 | 4.4 | 3.3 | 3.5 | 1.7 | 1.7 |

Example 18

Treatment as a Foam of Chicken Transport Cages with 3% Levulinic Acid Plus 2% SDS at 21° C.: Before Chemical Treatment

*Salmonella* isolation rate was 19% (19/100); fecal coliform population averaged 6.8 CFU/25 $cm^2$ log (3-9.3 log CFU/25 $cm^2$); total aerobic bacteria count averaged 7.9 log CFU/25 $cm^2$ (5.7-9.9 log CFU/25 $cm^2$); After treatment with 3% levulinic acid plus 2% SDS as a foam: *Salmonella* isolation rate was 1% (1/100); fecal coliform population averaged 1.15 log CFU/25 $cm^2$ (0.6-3.1 log CFU/25 $cm^2$), a 5.6 log CFU/25 $cm^2$ reduction; aerobic bacteria count averaged 4.8 log CFU/$cm^2$ (1.6-7.5 log CFU/25 $cm^2$), 3.2 log reduction.

Example 19

TABLE 36

*Salmonella* counts on whole chicken with feathers treated with tap water (soaked in 72 L) at 21° C. for 5 min

| | *Salmonella* counts (log CFU/9 $cm^2$) before and after treatment chicken number | | | | | | | | | |
|---|---|---|---|---|---|---|---|---|---|---|
| | 1 | | 2 | | 3 | | 4 | | 5 | |
| Location | before | after | before | after | before | after | before | after | before | after |
| Left wing | | 7.7 | | 6.8 | | 7.2 | | 7.6 | | 7.1 |
| Right wing | | 7.5 | | 6.9 | | 6.9 | | 7.4 | | 7.5 |
| Left breast | 8.4 | 7.4 | 8.3 | 7.3 | 8.2 | 6.4 | 8.0 | 8.5 | 8.0 | 7.1 |
| Right breast | | 8.2 | | 7.1 | | 7.3 | | 7.3 | | 6.9 |
| Neck | | 7.7 | | 6.8 | | 6.8 | | 8.4 | | 7.1 |

Example 20

TABLE 37

*Salmonella* counts on whole chickens with feathers treated with 50 ppm calcium hypochlorite (soaked in 72 L) at 21° C. for 5 min

| | *Salmonella* counts (log CFU/9 $cm^2$) before and after treatment chicken number | | | | | | | | | |
|---|---|---|---|---|---|---|---|---|---|---|
| | 1 | | 2 | | 3 | | 4 | | 5 | |
| Location | before | after | before | after | before | after | before | after | before | after |
| Left wing | | 8.0 | | 8.1 | | 8.8 | | 8.5 | | 7.6 |
| Right wing | | 8.0 | | 7.6 | | 8.4 | | 8.0 | | 8.4 |
| Left breast | 8.7 | 8.7 | 8.3 | 7.9 | 7.9 | 8.1 | 8.2 | 7.9 | 8.1 | 7.0 |
| Right breast | | 8.3 | | 8.0 | | 8.5 | | 7.8 | | 7.9 |
| Neck | | 8.9 | | 8.5 | | 7.9 | | 8.1 | | 7.9 |

Example 21

TABLE 38

Salmonella counts on whole chicken with feathers treated with 3% levulinic acid plus 2% SDS (soaked in 72 L) at 21° C. for 5 min

| | *Salmonella* counts (log CFU/9 $cm^2$) before and after treatment chicken number | | | | | | | | | |
|---|---|---|---|---|---|---|---|---|---|---|
| | 1 | | 2 | | 3 | | 4 | | 5 | |
| Location | before | after | before | after | before | after | before | after | before | after |
| Left wing | | <1.7 | | <1.7 | | <1.7 | | <1.7 | | <1.7 |
| Right wing | | <1.7 | | <1.7 | | <1.7 | | <1.7 | | <1.7 |
| Left breast | 8.8 | <1.7 | 8.3 | <1.7 | 8.0 | <1.7 | 8.3 | 3.1 | 8.7 | <1.7 |
| Right breast | | <1.7 | | 2.3 | | <1.7 | | <1.7 | | 2.8 |
| Neck | | 2.2 | | <1.7 | | <1.7 | | <1.7 | | <1.7 |

Example 22

TABLE 39

Salmonella counts on whole chickens with feathers treated with 3% levulinic acid plus 2% SDS (soaked in 72 L) at 55° C. for 5 min

| | *Salmonella* counts (log CFU/9 $cm^2$) before and after treatment chicken number | | | | | | | | | |
|---|---|---|---|---|---|---|---|---|---|---|
| | 1 | | 2 | | 3 | | 4 | | 5 | |
| Location | before | after | before | after | before | after | before | after | before | after |
| Left wing | | 3.9 | | 4.1 | | 3.4 | | 6.0 | | 4.1 |
| Right wing | | <1.7 | | 5.5 | | 5.5 | | 3.8 | | 4.0 |
| Left breast | 7.7 | 4.3 | 7.6 | 5.1 | 7.7 | 5.0 | 7.6 | 4.0 | 7.1 | 5.3 |
| Right breast | | 2.7 | | 4.6 | | 4.6 | | 3.1 | | 3.6 |
| Neck | | 2.6 | | 4.5 | | 4.1 | | 4.2 | | 4.4 |

What is claimed is:

1. A method of reducing a microbial population on the surface of a non-liquid foodstuff, wherein the method comprises the step of contacting the foodstuff with an antimicrobial composition, said antimicrobial composition consisting of a monoprotic organic acid having a carbon backbone of 4 to 10 carbons, a surfactant, and a solvent, for a time effective in reducing the viability or the cell density of the microbial population on the surface of a foodstuff, wherein the total concentration of the monoprotic organic acid is about 0.1% to about 3% by weight per volume of the antimicrobial composition, and the surfactant is about 0.1 to 2% by weight per volume of the antimicrobial composition.

2. The method of claim 1, wherein the monoprotic organic acid is levulinic acid.

3. The method of claim 1, wherein the surfactant is selected from the group consisting of: sodium dodecyl sulfate, sodium laureth sulfate, a quaternary ammonium cation, cetyl pyridinium chloride, and benzalkonium chloride.

4. The method of claim 3, wherein the surfactant is sodium dodecyl sulfate.

5. The method of claim 1, wherein the monoprotic organic acid is levulinic acid and the surfactant is sodium dodecyl sulfate.

6. The method of claim 1, wherein the composition comprises about 0.3 to about 3% levulinic acid by weight per volume of the antimicrobial composition, and about 0.05% to about 2% sodium dodecyl sulfate by weight per volume of the antimicrobial composition.

7. The method of claim 1 wherein the antimicrobial composition is delivered to the non-liquid foodstuff as a wash, a spray, or a foam.

8. The method of claim 1, wherein the foodstuff is a raw foodstuff, a processed foodstuff, a packaged foodstuff, or any combination thereof.

9. The method of claim 8, wherein the foodstuff is a plant part, a vegetable product, or any combination thereof.

10. The method of claim 8, wherein the foodstuff is a whole animal, an animal carcass, a part thereof, an animal product, an egg, a processed animal product, or any combination thereof.

11. The method of claim 9, wherein the foodstuff is a leaf, a seed, a nut, a fruit, a processed leaf, a processed seed, a processed nut, a processed fruit, or any combination thereof.

12. The method of claim 1, wherein the method provides a processed foodstuff with antibacterial qualities, said method comprising combining the antimicrobial composition with a raw food material to form a mixture; and processing said mixture to form a processed foodstuff.

13. The method of claim 12, wherein the raw food material is an unprocessed meat and said mixture is then ground.

14. The method of claim 12 wherein the raw food material is shelved nuts to form a mixture, and said mixture is then ground for the preparation of a nut butter.

15. The method of claim 1, wherein the antimicrobial composition is added to a package with said non-liquid foodstuff.

* * * * *